(12) United States Patent
Emamian

(10) Patent No.: US 8,541,670 B2
(45) Date of Patent: Sep. 24, 2013

(54) COMPOSITIONS AND METHODS FOR INHIBITING TUMOR CELL GROWTH

(76) Inventor: Effat Emamian, Short Hills, NJ (US)

( * ) Notice: Subject to any disclaimer, the term of this patent is extended or adjusted under 35 U.S.C. 154(b) by 865 days.

(21) Appl. No.: 12/560,914

(22) Filed: Sep. 16, 2009

(65) Prior Publication Data

US 2010/0047226 A1    Feb. 25, 2010

Related U.S. Application Data

(63) Continuation of application No. PCT/US2008/057572, filed on Mar. 20, 2008.

(60) Provisional application No. 60/896,072, filed on Mar. 21, 2007.

(51) Int. Cl.
*C07K 7/00*    (2006.01)

(52) U.S. Cl.
CPC .................................... *C07K 7/00* (2013.01)
USPC ........................................................ 930/250

(58) Field of Classification Search
None
See application file for complete search history.

(56) References Cited

U.S. PATENT DOCUMENTS

2006/0172378 A1    8/2006  Levine et al.
2012/0034651 A1*   2/2012  Noguchi et al. ............. 435/69.1

FOREIGN PATENT DOCUMENTS

WO    WO04001384 A2      12/2003
WO    WO2005010174 A2     2/2005
WO    WO2005056594    *   6/2005

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
"Extended European Search Report" for EP Patent App. No. 08732515.5; Feb. 10, 2011.

* cited by examiner

*Primary Examiner* — Sheridan Swope
(74) *Attorney, Agent, or Firm* — McCarter & English LLP; Bryan Zerhusen; Gabriel J. McCool

(57) ABSTRACT

The present invention relates to compositions and methods for inhibiting the activity of an enzyme, for example, Protein Kinase B, p70S6K and/or Abl using the catalytic subunit of Protein Kinase A (PKAc), or at least one PKAc fragment or variant PKAc fragment thereof. In this regard, methods for preventing or treating cancer or a neurodegenerative disease or disorder are also provided.

8 Claims, 3 Drawing Sheets

```
             1                                                           50
Human 1   MGNAAAAKKG SEQESVKEFL AKAKEDFLKK WESPAQNTAH LDQFERIKTL
Bovine    MGNAAAAKKG SEQESVKEFL AKAKEDFLKK WENPAQNTAH LDQFERIKTL
Mouse     MGNAAAAKKG SEQESVKEFL AKAKEDFLKK WETPSQNTAQ LDQFDRIKTL
Rat       MGNAAAAKKG SEQESVKEFL AKAKEDFLKK WEDPSQNTAQ LDHFDRIKTL
Canine    MGNAAA.KKG SEQESVKEFL AKAKEDFLKK WENPAQNTAH LDQFERIKTL
Human 2   ........MA SNSSDVKEFL AKAKEDFLKK WESPAQNTAH LDQFERIKTL
Consen.   ........XX S#XXXVKEFL AKAKEDFLKK WEXPXQNTAX LDXF#RIKTL
             G-LOOP
          51‾‾‾‾‾‾‾                                                     100
Human 1   GTGSFGRVML VKHKETGNHY AMKILDKQKV VKLKQIEHTL NEKRILQAVN
Bovine    GTGSFGRVML VKHMETGNHY AMKILDKQKV VKLKQIEHTL NEKRILQAVN
Mouse     GTGSFGRVML VKHKESGNHY AMKILDKQKV VKLKQIEHTL NEKRILQAVN
Rat       GTGSFGRVML VKHKESGNHY AMKILDKQKV VKLKQIEHTL NEKRILQAVN
Canine    GTGSFGRVML VKHKETGNHF AMKILDKQKV VKLKQIEHTL NEKRILQAVN
Human 2   GTGSFGRVML VKHKETGNHY AMKILDKQKV VKLKQIEHTL NEKRILQAVN
Consen.   GTGSFGRVML VKHXEtGNH% AMKILDKQKV VKLKQIEHTL NEKRILQAVN 101                                                        150
Human 1   FPFLVKLEFS FKDNSNLYMV MEYVPGGEMF SHLRRIGRFS EPHARFYAAQ
Bovine    FPFLVKLEFS FKDNSNLYMV MEYVPGGEMF SHLRRIGRFS EPHARFYAAQ
Mouse     FPFLVKLEFS FKDNSNLYMV MEYVAGGEMF SHLRRIGRFS EPHARFYAAQ
Rat       FPFLVKLEFS FKDNSNLYMV MEYVPGGEMF SHLRRIGRFS EPHARFYAAQ
Canine    FPFLVKLEFS FKDNSNLYMV MEYVPGGEMF SHLRRIGRFS EPHARFYAAQ
Human 2   FPFLVKLEFS FKDNSNLYMV MEYVPGGEMF SHLRRIGRFS EPHARFYAAQ
Consen.   FPFLVKLEFS FKDNSNLYMV MEYVXGGEMF SHLRRIGRFS EPHARFYAAQ
                         CATALYTIC L   OOP           ACTIVATION LOOP
             151        ‾‾‾‾‾‾‾‾‾‾‾‾‾‾‾‾‾           ‾‾‾‾‾‾‾‾‾‾‾‾‾‾‾‾    200
Human 1   IVLTFEYLHS LDLIYRDLKP ENLLIDQQGY IQVTDFGFAK RVKGRTWTLC
Bovine    IVLTFEYLHS LDLIYRDLKP ENLLIDQQGY IQVTDFGFAK RVKGRTWTLC
Mouse     IVLTFEYLHS LDLIYRDLKP ENLLIDQQGY IQVTDFGFAK RVKGRTWTLC
Rat       IVLTFEYLHS LDLIYRDLKP ENLLIDQQGY IQVTDFGFAK RVKGRTWTLC
Canine    IVLTFEYLHS LDLIYRDLKP ENLLIDQQGY IQVTDFGFAK RVKGRTWTLC
Human 2   IVLTFEYLHS LDLIYRDLKP ENLLIDQQGY IQVTDFGFAK RVKGRTWTLC
Consen.   IVLTFEYLHS LDLIYRDLKP ENLLIDQQGY IQVTDFGFAK RVKGRTWTLC 201‾‾‾                                                     250
Human 1   GTPEYLAPEI ILSKGYNKAV DWWALGVLIY EMAAGYPPFF ADQPIQIYEK
Bovine    GTPEYLAPEI ILSKGYNKAV DWWALGVLIY EMAAGYPPFF ADQPIQIYEK
Mouse     GTPEYLAPEI ILSKGYNKAV DWWALGVLIY EMAAGYPPFF ADQPIQIYEK
Rat       GTPEYLAPEI ILSKGYNKAV DWWALGVLIY EMAAGYPPFF ADQPIQIYEK
Canine    GTPEYLAPEI ILSKGYNKAV DWWALGVLIY EMAAGYPPFF ADQPIQIYEK
Human 2   GTPEYLAPEI ILSKGYNKAV DWWALGVLIY EMAAGYPPFF ADQPIQIYEK
Consen.   GTPEYLAPEI ILSKGYNKAV DWWALGVLIY EMAAGYPPFF ADQPIQIYEK 251                                                        300
Human 1   IVSGKVRFPS HFSSDLKDLL RNLLQVDLTK RFGNLKNGVN DIKNHKWFAT
Bovine    IVSGKVRFPS HFSSDLKDLL RNLLQVDLTK RFGNLKNGVN DIKNHKWFAT
Mouse     IVSGKVRFPS HFSSDLKDLL RNLLQVDLTK RFGNLKNGVN DIKNHKWFAT
Rat       IVSGKVRFPS HFSSDLKDLL RNLLQVDLTK RFGNLKNGVN DIKNHKWFAT
Canine    IVSGKVRFPS HFSSDLKDLL RNLLQVDLTK RFGNLKNGVN DIKNHKWFAT
Human 2   IVSGKVRFPS HFSSDLKDLL RNLLQVDLTK RFGNLKNGVN DIKNHKWFAT
Consen.   IVSGKVRFPS HFSSDLKDLL RNLLQVDLTK RFGNLKNGVN DIKNHKWFAT 301                                                        350
Human 1   TDWIAIYQRK VEAPFIPKFK GPGDTSNFDD YEEEEIRVSI NEKCGKEFSE
Bovine    TDWIAIYQRK VEAPFIPKFK GPGDTSNFDD YEEEEIRVSI NEKCGKEFSE
Mouse     TDWIAIYQRK VEAPFIPKFK GPGDTSNFDD YEEEEIRVSI NEKCGKEFTE
Rat       TDWIAIYQRK VEAPFIPKFK GPGDTSNFDD YEEEEIRVSI NEKCGKEFTE
Canine    TDWIAIYQRK VEAPFIPKFK GPGDTSNFDD YEEEEIRVSI NEKCGKEFCE
Human 2   TDWIAIYQRK VEAPFIPKFK GPGDTSNFDD YEEEEIRVSI NEKCGKEFSE
Consen.   TDWIAIYQRK VEAPFIPKFK GPGDTSNFDD YEEEEIRVSI NEKCGKEFXE 351
Human 1   F  (SEQ ID NO:1)
Bovine    F  (SEQ ID NO:3)
Mouse     F  (SEQ ID NO:5)
Rat       F  (SEQ ID NO:6)
Canine    F  (SEQ ID NO:4)           FIG. 4
Human 2   F  (SEQ ID NO:2)
Consen.   F  (SEQ ID NO:7)
```

COMPOSITIONS AND METHODS FOR INHIBITING TUMOR CELL GROWTH

CROSS-REFERENCE TO RELATED APPLICATIONS

This application is a continuation of International PCT Application No. PCT/US2008/057572, having an international filing date of Mar. 20, 2008, which claims the benefit of U.S. Provisional Patent Application Ser. No. 60/896,072, filed Mar. 21, 2007, the disclosures each of which are hereby incorporated by reference in their entireties.

SEQUENCE LISTING

The present application hereby incorporates by reference, in its entirety, the Electronic/Computer Readable Form of the Sequence Listing, filed herewith, which is identical to the listing of sequences submitted to the United States Patent and Trademark Office in association with U.S. Provisional Patent Application Ser. No. 60/895,072; filed Mar. 21, 2007; and contains no new matter. The Sequence Listing contains amino acid sequences, SEQ. ID NO. 1-104, in file: "Emamian_PCT_seqlist_ST25.txt;" created: 18 Mar. 2008; using PatentIn 3.4 software; OS: MS Windows XP; size: 51 KB.

STATEMENT REGARDING FEDERALLY SPONSORED RESEARCH

The U.S. Government has certain rights in this invention pursuant to Grant No.: 5R01-MH039327; entitled: Synapsins—Regulators of Neurotransmitter Release, awarded by the National Institutes of Health (NIH).

FIELD OF THE INVENTION

The present invention relates to therapeutic polypeptide compositions and methods of administration to an organism in need thereof for treating and/or preventing disease, for example, cancer.

BACKGROUND OF THE INVENTION

The serine-threonine kinase AKT (known also as Protein Kinase B) phosphorylates various protein substrates to regulate many key physiological processes, such as cell cycle, glucose metabolism, cell growth and survival, angiogenesis and protein synthesis (Brazil, et al. (2002) *Cell* 111:293-303). Stimulation of its catalytic activity is triggered by phosphatidylinositol 3 kinase and results from the PtdIns(3,4,5)P-dependent recruitment of AKT, from the cytoplasm to the membrane, as well as the phosphorylation of two regulatory residues, Thr-308 and Ser-473. Phosphorylation of Thr-308, catalyzed by PDK-1, is required for AKT activity, and this activity is augmented, ~10 fold, by Ser-473 phosphorylation (Alessi, et al. (1996) *EMBO J.* 15:6541-6551; Brazil, et al. (2002) supra).

Protein Kinase A (PKA) is ubiquitously expressed in mammalian cells and regulates important cellular processes such as growth, development, memory, metabolism, gene expression, and lipolysis. The PKA holoenzyme exists as an inactive complex and is composed of two catalytic (PKAc) and regulatory (PKA RI & RII) subunits. Binding of cAMP facilitates the dissociation and activation of catalytic subunits. Each catalytic subunit is composed of a small and large lobe, with the active site forming a cleft between the two lobes. The small lobe provides the binding site for ATP, and the large lobe provides catalytic residues and a docking surface for peptide/protein substrates. The activation loop in the large lobe contains a phosphorylation site, Thr-197, which is essential for catalysis (Adams, et al. (1995) *Biochemistry* 34:2447-2454).

Deregulation of AKT signaling pathway is known to be directly associated with some of the most prevalent and incurable human disorders such as cancer, neurodegenerative and psychiatric brain disorders (Blain and Massague (2002) *Nat. Med.* 8:1076-1078; Brazil, et al. (2004) *Trends Biochem. Sci.* 29:233-242; Chen, et al. (2003) *Cell* 113:457-468; Colin, et al. (2005) *Eur. J. Neurosci.* 21:1478-1488; Emamian, et al. (2004) *Nat. Genetics* 36:131-137; Griffin, et al. (2005) *J. Neurochem.* 93:105-117; Liang, et al. (2002) *Nat. Med.* 8:1153-1160; Shin, et al. (2002) *Nat. Med.* 8:1145-1152; Viglietto, et al. (2002) *Nat. Med.* 8:1136-1144). It is well-established that the hyperactivity of AKT is part of the pathologic process in several types of the most prevalent human malignancies (Brazil, et al. (2004) supra), including breast cancer, prostate cancer, lung cancer, gastrointestinal tumors, pancreatic cancer, hepatocellular carcinoma, thyroid cancer, and central nervous system malignancies (such as glioblastoma and gliomas). Association of AKT function with several neurodegenerative brain disorders such as the Alzheimer's disease (AD), Huntington's disease (HD), spinocerebellar ataxia type 1 (SCA1), and amyotrophic lateral sclerosis (ALS), have also been reported (Griffin, et al. (2005) supra; Colin, et al. (2005) supra; Saudou, et al. (1998) *Cell* 95:55-66; Chen, et al. (2003) supra; Emamian, et al. (2003)*Neuron* 38:375-387; Kaspar, et al. (2003)*Science* 301:839-842).

An impairment in the AKT signaling pathway is also involved in schizophrenia (Emamian, et al. (2004) supra). The genetic association of AKT1 gene with schizophrenia has been identified in European (Schwab, et al. (2005) *Biol. Psychiatry* 58:446-450) and Japanese (Ikeda, et al. (2004) *Biol. Psychiatry* 56:698-700) populations. Moreover, the PKA signaling pathway has been found to mediate the interaction of DISC1 and PDE4B, genetic factors known to be associated with higher risk for schizophrenia (Millar, et al. (2005) *Science* 310:1187-1191).

Given the association of AKT with some of the most prevalent and incurable human diseases, including cancer, neurodegenerative and psychiatric disorders, there is a need in the art to identify agents which interact with and modulate the activity of AKT. The present invention meets this need in the art.

SUMMARY

The present invention is a pharmaceutical composition containing the catalytic subunit of Protein Kinase A (PKAc), or at least one PKAc fragment or variant PKAc fragment thereof, in admixture with a pharmaceutically acceptable carrier.

The present invention is also a moiety for targeted delivery of a therapeutic agent to a cell, wherein said moiety is a PKAc fragment or variant PKAc fragment thereof.

Also included are methods for inhibiting the activity of at least one enzyme selected from the group consisting of Protein Kinase B, p70S6K, and Abl; and inhibiting cell proliferation are also provided, as are methods for preventing or treating cancer or a neurodegenerative disease or disorder.

BRIEF DESCRIPTION OF THE DRAWINGS

FIG. 4 depicts an amino acid sequence alignment of PKAc proteins isolated from human (isoforms 1 and 2), bovine, rat, mouse, bovine, and canine sources. Amino acid residues common amongst mammalian PKAc proteins are indicated in the consensus sequence. Symbols in the consensus sequence are as follows: x denotes any amino acid residue; % denotes Phe or Tyr; and # denotes Asn, Asp, Gln, or Glu. The solid bars above the sequences indicate the G loop, catalytic loop, and activation loop, respectively. See, e.g., Abel, et al. (2001) *J. Biol. Chem.* 276:10320-10329; Kim, et al. (2005) *Science* 307:690696). Thr-197 is indicated in bold.

DETAILED DESCRIPTION

Figure 1:
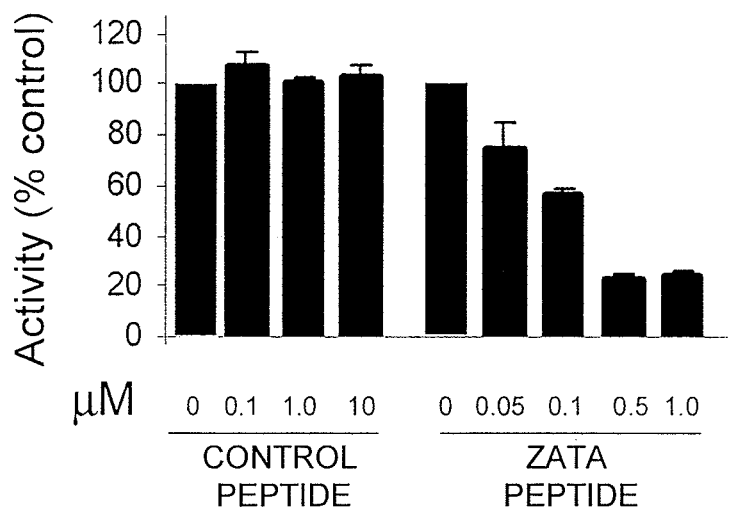
FIG. 1 shows that the ZaTa peptide, flanking Thr-197 of PKAc, is sufficient to inhibit AKT activity. AKT1 catalytic activity was determined by measuring the incorporation of $-^{32}P$ into Ser-21 glycogen synthase kinase 3□ (GSK-3□) substrate peptide. Histogram bars represent the number of $-^{32}P$ counts per minute (CPM). Reactions were carried out in the presence of different concentrations of the ZaTa peptide (SEQ ID NO:60), as well as a control peptide (SEQ ID NO:59) which shares 11 out of 17 amino acids in common with the N-terminus of the ZaTa peptide. IC-50 of the ZaTa peptide was within a nanomolar range in these assays.

AKT has emerged as the focal point of many signal transduction pathways, regulating multiple cellular processes such as glucose metabolism, transcription, apoptosis, cell proliferation, angiogenesis, and cell motility (Brazil, et al. (2002) supra). Besides functioning as a kinase of many substrates involved in these processes, it forms complexes with other proteins that are not substrates, wherein the other proteins modulate AKT activity and function (Brazil, et al. (2002) supra).

As used here, the terms "peptide," "polypeptide," and "protein" are used interchangeably, and refer to any molecule having at least two amino acids, amino acid analogs or derivatives linked by a peptide bond or other covalent bond.

A novel physical interaction between AKT and PKAc has now been identified. Full-length PKAc was found to potently inhibit the catalytic activity of AKT, while active AKT increased the catalytic activity of PKA through a mechanism that increased the phosphorylation level of PKAc at Thr-197. Unexpectedly, short PKAc fragments could also modulate AKT. Some peptides were found to activate AKT, while others inhibited AKT activity. In particular, a PKAc fragment flanking Thr-197 of PKAc, designated herein as ZaTa, was sufficient to potently inhibit AKT in vitro and in vivo. ZaTa penetrated into the cell, co-localized with AKT, inhibited and redistributed AKT within the cell, and changed the expression pattern of PKAc. ZaTa also disrupted the AKT-PKAc complex, both in vitro and in vivo, which resulted in substantial changes in neurite and axon morphology. Treatment of cultured cells with ZaTa caused a dose-dependent inhibition of cell proliferation as well. Furthermore, reducing PKAc protein level increased the AKT protein level in vitro and in vivo. Accordingly, PKAc and fragments thereof are useful for modulating AKT signal transduction pathways involved in regulating glucose metabolism, transcription, apoptosis, cell proliferation, angiogenesis, and cell motility thereby facilitating the prevention or treatment of cancer, neurodegenerative and psychiatric disorders.

To identify proteins that directly interact with AKT, co-immunoprecipitation assays were performed to purify AKT from the brain lysate. Co-immunoprecipitated proteins were separated by sodium dodecyl sulfate-polyacrylamide gel electrophoresis (SDS-PAGE) and analyzed by mass spectrometry. Using this approach, the catalytic subunit of PKA (PKAc) was identified as an AKT interacting protein. In several independent co-immunoprecipitation experiments using two different antibodies that recognized distinct epitopes on the AKT sequence, i.e., one antibody recognized phosphorylated AKT at Ser-473 and the other antibody was raised against the pleckstrin homology (PH) domain of AKT, PKAc was detected in complex with AKT as determined by western blot analysis with an antibody against PKAc. Unexpectedly, a higher amount of PKAc was immunoprecipitated in complex with AKT when the sample was treated with cAMP, which increased the level of unbound PKAc to the regulatory subunits. These data demonstrate a physical interaction between endogenous PKAc and AKT, wherein the interaction occurs after activation of PKA.

To demonstrate that PKAc and AKT co-localize, subcellular localization of PKAc and AKT was analyzed by immunofluorescence confocal microscopy. Neuroblastoma 2a (N2a) neurons expressing an endogenous level of AKT and PKAc were double-labeled with anti-AKT (PH domain) and anti-PKAc antibodies. The strongest signal for the endogenous level of both molecules in cultured N2a cells was detected along the neurite and on the neurite outgrowth zone. However, NG-108 neurons, a somatic cell hybrid of glioblastoma and neuroblastoma, showed a more diffuse pattern of co-localization in the cytoplasm and a weaker signal in neurites. These data confirmed the results of the co-immunoprecipitation experiments and indicated a role for the AKT and PKAc interaction in the growth and branching of neuronal cell processes. The co-localization of AKT and PKAc in non-neuronal cell lines derived from the normal and malignant cells of human breast tissue was also determined. The cell lines analyzed were HTB-126 cells derived from an infiltrating ductal carcinoma, HTB-125 cells derived from normal breast tissue peripheral to the infiltrating ductal carcinoma, and CRL-2865 cells derived from the pleural effusion metastatic site of a patient with breast ductal carcinoma. In these cells, endogenous AKT co-localized with the endogenous PKAc in specific subcellular compartments of both normal and malignant human breast cells. AKT appeared to co-localize with PKAc in a microtubule-like structure adjacent to nuclei (both HTB-125 and HTB-126) and on the cell membrane (HTB-125).

These data indicated that the AKT-PKAc interaction was not specific to neuronal cells and occurred in normal and malignant cell lines derived from human tissue as well.

To evaluate the significance of the AKT-PKAc interaction, kinase inhibitors were employed. Unlike AKT, for which direct and specific inhibitors/activators are not readily available, highly selective and well-characterized PKA inhibitors and activators are well-known in the art. Thus, cultured neurons were treated with the selective PKA inhibitor, H-89, and the potent PKA activator, forskolin, and AKT activity was analyzed. Treatment with the PKA inhibitor caused a dose-dependent increase in the activity of AKT, whereas the PKA activator had an opposing effect, measured by the activation-dependent phosphorylation level of AKT at both Thr-308 and Ser-473 sites. These findings indicated that the level of AKT activity in cultured neurons was tightly and inversely correlated with the level of PKA activity.

Since the observed effect of H-89 and forskolin on AKT activity in cultured cells could be interpreted as the result of the regulatory interference of other signaling pathways, in vitro analysis was carried using purified, active forms of AKT and PKAc to examine the direct result of this interaction on the kinase catalytic activity. When a full-length, active PKAc was added to AKT kinase assays containing active AKT as the kinase and Ser-9 GSK-3 glutathione (GST) fusion protein as the substrate, the kinetic activity of AKT was dramatically reduced. This decrease in the catalytic activity of AKT by PKAc was inhibited when the PKA inhibitor was added to the reaction mixture. This observation indicated that the activity of PKA was required for its inhibitory effect on AKT. The decrease in the catalytic activity of AKT by PKAc was also observed with two mutants and active forms of AKT1, one with a deletion in the PH domain and the other one with a Ser473Asp mutation. As with wild-type AKT, the inhibitory effect of PKAc on the mutants was reversed in the presence of the PKA inhibitor peptide. This indicated that the PH domain of AKT, as well as the phosphorylation at Ser-473, were not required for the inhibitory effect of PKAc toward AKT. Further, the same inhibitory effect was observed with active PKAc purified from bovine tissue, or with human PKAc expressed in Sf9 cells, regardless of the presence or absence of phosphatase inhibitors in the kinase reaction.

The effect of AKT on the catalytic activity of PKA was further analyzed using an in vitro kinase assay containing PKAc as the kinase and DARPP-32 as the substrate. PKA phosphorylates DARPP-32 at the Thr-34 site, converting it into a potent inhibitor of protein phosphatase-1 (Huang, et al. (1999) *J. Biol. Chem.* 274:7870-7878). In contrast to the inhibitory role of PKAc on the AKT catalytic activity, addition of the active AKT to the PKA kinase assay increased the catalytic activity of PKAc. This was determined by measuring the phosphorylation level of DARPP-32 at Thr-34, using a phospho-specific antibody against this site. Unexpectedly, the increase in the PKAc catalytic activity was accompanied by an increase in the phosphorylation level of PKAc at Thr-197, a residue located in the activation loop of PKAc which is essential for proper biological function and possibly cell motility (Abel, et al. (2001) supra; Cheng, et al. (1998) *Proc. Natl. Acad. Sci. USA* 95:9849-9854). While autophosphorylation and phosphorylation by PDK-1 have been described as possible mechanisms for this phosphorylation of Thr-197 in PKAc (Moore, et al. (2002) *J. Biol. Chem.* 277:47878-47884), the in vitro data disclosed herein indicates that AKT phosphorylates Thr-197 of PKAc. Similar opposing effects on the catalytic activity were observed when kinase reactions were conducted in the presence of the both PKAc and AKT specific substrates in the same reaction tube. In control assays, neither the phosphorylation of Ser-9 GSK-3 GST fusion protein by PKAc, nor the phosphorylation at Thr-34 of the recombinant DARPP-32 by AKT was observed.

Unlike PKAc and protein kinase C (PKC) for which potent inhibitor peptides are readily available and widely used, inhibitors of AKT are generally lacking (Brazil, et al. (2004) supra). It has been empirically shown that the use of PKA mutants can facilitate the structural design of more selective inhibitors for AKT (Breitenlechner, et al. (2005) *J. Med. Chem.* 48:163-170). Moreover, optimal substrate motifs for AKT have been modified to design AKT inhibitors (Obata, et al. (2000) *J. Biol. Chem.* 275:36108-36115). Because the full-length PKAc protein inhibited the catalytic activity of AKT, a peptide library based on the human (GENBANK Accession No. NP_002721; SEQ ID NO:1) and bovine (GENBANK Accession No. CAA47627; SEQ ID NO:2) PKAc protein sequences was designed and synthesized. This library contained 96 overlapping peptides (Table 1), covering the full-length protein sequence of human and bovine PKAc from the N- to C-terminus. The library was extensively screened to identify fragments of PKAc that mediated the inhibitory effect of PKAc toward AKT.

TABLE 1

| Peptide | Molecular Weight | Sequence | SEQ ID NO: |
|---|---|---|---|
| 1 | 1577.9 | M-G-N-A-A-A-A-K-K-G-S-E-Q-E-S-V | 8 |
| 2 | 1651 | A-A-K-K-G-S-E-Q-E-S-V-K-E-F-L | 9 |
| 3 | 1651 | G-S-E-Q-E-S-V-K-E-F-L-A-K-A-K | 10 |
| 4 | 1754.2 | E-S-V-K-E-F-L-A-K-A-K-E-D-F-L | 11 |
| 5 | 1753.3 | E-F-L-A-K-A-K-E-D-F-L-K-K-W | 12 |
| 6 | 1775.2 | A-K-A-K-E-D-F-L-K-K-W-E-N-P-A | 13 |
| 7 | 1791 | E-D-F-L-K-K-W-E-N-P-A-Q-N-T-A | 14 |
| 8 | 1536.7 | K-K-W-E-N-P-A-Q-N-T-A-H-L | 15 |
| 9 | 1670.7 | W-E-N-P-A-Q-N-T-A-H-L-D-Q-F | 16 |
| 10 | 1768 | P-A-Q-N-T-A-H-L-D-Q-F-E-R-I-K | 17 |

TABLE 1-continued

| Peptide | Molecular Weight | Sequence | SEQ ID NO: |
|---|---|---|---|
| 11 | 1571.9 | T-A-H-L-D-Q-F-E-R-I-K-T-L | 18 |
| 12 | 1849.3 | H-L-D-Q-F-E-R-I-K-T-L-G-T-G-S-F | 19 |
| 13 | 1652.2 | E-R-I-K-T-L-G-T-G-S-F-G-R-V-M | 20 |
| 14 | 1603.1 | T-L-G-T-G-S-F-G-R-V-M-L-V-K-H | 21 |
| 15 | 1361.8 | G-S-F-G-R-V-M-L-V-K-H-M | 22 |
| 16 | 1843.2 | S-F-G-R-V-M-L-V-K-H-M-E-T-G-N-H | 23 |
| 17 | 1790.2 | M-L-V-K-H-M-E-T-G-N-H-Y-A-M-K | 24 |
| 18 | 1788.2 | H-M-E-T-G-N-H-Y-A-M-K-I-L-D-K | 25 |
| 19 | 1744.2 | G-N-H-Y-A-M-K-I-L-D-K-Q-K-V-V | 26 |
| 20 | 1642.3 | A-M-K-I-L-D-K-Q-K-V-V-K-L-K | 27 |
| 21 | 1819.3 | I-L-D-K-Q-K-V-V-K-L-K-Q-I-E-H | 28 |
| 22 | 1692.1 | K-Q-K-V-V-K-L-K-Q-I-E-H-T-L | 29 |
| 23 | 1835.2 | V-V-K-L-K-Q-I-L-H-T-L-N-E-K-R | 30 |
| 24 | 1821.2 | K-Q-I-L-H-T-L-N-E-K-R-I-L-Q-A | 31 |
| 25 | 1683 | H-T-L-N-E-K-R-I-L-Q-A-V-N-F | 32 |
| 26 | 1788.2 | N-E-K-R-I-L-Q-A-V-N-F-P-F-L-V | 33 |
| 27 | 1778.3 | I-L-Q-A-V-N-F-P-F-L-V-K-L-E-F | 34 |
| 28 | 1715.2 | V-N-F-P-F-L-V-K-L-E-F-S-F-K | 35 |
| 29 | 1898.4 | P-F-L-V-K-L-E-F-S-F-K-D-N-S-N-L | 36 |
| 30 | 1838.3 | L-E-F-S-F-K-D-N-S-N-L-Y-M-V-M | 37 |
| 31 | 1753.1 | F-K-D-N-S-N-L-Y-M-V-M-E-Y-V | 38 |
| 32 | 1834.2 | N-S-N-L-Y-M-V-M-E-Y-V-P-G-G-E-M | 39 |
| 33 | 1727.1 | M-V-M-E-Y-V-P-G-G-E-M-F-S-H-L | 40 |
| 34 | 1662.1 | Y-V-P-G-G-E-M-F-S-H-L-R-R-I | 41 |
| 35 | 1663.2 | G-G-E-M-F-S-H-L-R-R-I-G-R-F | 42 |
| 36 | 1870.3 | M-F-S-H-L-R-R-I-G-R-F-S-E-P-H | 43 |
| 37 | 1905.4 | L-R-R-I-G-R-F-S-E-P-H-A-R-F-Y | 44 |
| 38 | 1750.1 | G-R-F-S-E-P-H-A-R-F-Y-A-A-Q-I | 45 |
| 39 | 1763.1 | E-P-H-A-R-F-Y-A-A-Q-I-V-L-T-F | 46 |
| 40 | 1871.3 | R-F-Y-A-A-Q-I-V-L-T-F-E-Y-L-H | 47 |
| 41 | 1762.2 | A-Q-I-V-L-T-F-E-Y-L-H-S-L-D-L | 48 |
| 42 | 1783.3 | L-T-E-L-Y-H-S-L-D-L-I-Y-R | 49 |
| 43 | 1778.3 | E-Y-L-H-S-L-D-L-I-Y-R-D-L-K | 50 |
| 44 | 1826.3 | H-S-L-D-L-I-Y-R-D-L-K-P-E-N-L | 51 |
| 45 | 1600.2 | L-I-Y-R-D-L-K-P-E-N-L-L-I | 52 |
| 46 | 1965.4 | Y-R-D-L-K-P-E-N-L-L-I-D-Q-Q-G-Y | 53 |
| 47 | 1629.9 | P-E-N-L-L-I-D-Q-Q-G-Y-I-Q-V | 54 |
| 48 | 1653 | L-L-I-D-Q-Q-G-Y-I-Q-V-T-D-F | 55 |
| 49 | 1717 | D-Q-Q-G-Y-I-Q-V-T-D-F-G-F-A-K | 56 |

TABLE 1-continued

| Peptide | Molecular Weight | Sequence | SEQ ID NO: |
|---|---|---|---|
| 50 | 1672.1 | Y-I-Q-V-T-D-F-G-F-A-K-R-V-K | 57 |
| 51 | 1768.2 | V-T-D-F-G-F-A-K-R-V-K-G-R-T-W | 58 |
| 52 | 1520 | G-F-A-K-R-V-K-G-R-T-W-T-L | 59 |
| 53 | 1966.4 | A-K-R-V-K-G-R-T-W-T-L-C-G-T-P-E-Y | 60 |
| 54 | 1510.8 | R-T-W-T-L-C-G-T-P-E-Y-L-A | 61 |
| 55 | 1706.1 | W-T-L-C-G-T-P-E-Y-L-A-P-E-I-I | 62 |
| 56 | 1531 | G-T-P-E-Y-L-A-P-E-I-I-L-S-K | 63 |
| 57 | 1738.3 | E-Y-L-A-P-E-I-I-L-S-K-G-Y-N-K | 64 |
| 58 | 1733.2 | P-E-I-I-L-S-K-G-Y-N-K-A-V-D-W | 65 |
| 59 | 1651.1 | L-S-K-G-Y-N-K-A-V-D-W-W-A-L | 66 |
| 60 | 1705.2 | G-Y-N-K-A-V-D-W-W-A-L-G-V-L-I | 67 |
| 61 | 1737.2 | A-V-D-W-W-A-L-G-V-L-I-Y-E-M-A | 68 |
| 62 | 1557.1 | W-A-L-G-V-L-I-Y-E-M-A-A-G-Y | 69 |
| 63 | 1675.2 | G-V-L-I-Y-E-M-A-A-G-Y-P-P-F-F | 70 |
| 64 | 1363.7 | Y-E-M-A-A-G-Y-P-P-F-F-A | 71 |
| 65 | 1654 | E-M-A-A-G-Y-P-P-F-F-A-D-Q-P-I | 72 |
| 66 | 1656 | G-Y-P-P-F-F-A-D-Q-P-I-Q-I-Y | 73 |
| 67 | 1808.2 | P-F-F-A-D-Q-P-I-Q-I-Y-E-K-I-V | 74 |
| 68 | 1717.1 | D-Q-P-I-Q-I-Y-E-K-I-V-S-G-K-V | 75 |
| 69 | 1680.2 | I-Q-I-Y-E-K-I-V-S-G-K-V-R-F | 76 |
| 70 | 1794.2 | Y-E-K-I-V-S-G-K-V-R-F-P-S-H-F | 77 |
| 71 | 1663 | V-S-G-K-V-R-F-P-S-H-F-S-S-D-L | 78 |
| 72 | 1761.2 | V-R-F-P-S-H-F-S-S-D-L-K-D-L-L | 79 |
| 73 | 1758.3 | S-H-F-S-S-D-L-K-D-L-L-R-N-L-L | 80 |
| 74 | 1755.3 | S-D-L-K-D-L-L-R-N-L-L-Q-V-D-L | 81 |
| 75 | 1844.4 | D-L-L-R-N-L-L-Q-V-D-L-T-K-R-F | 82 |
| 76 | 1759.3 | N-L-L-Q-V-D-L-T-K-R-F-G-N-L-K | 83 |
| 77 | 1561 | V-D-L-T-K-R-F-G-N-L-K-N-G-V | 84 |
| 78 | 1704.2 | T-K-R-F-G-N-L-K-N-G-V-N-D-I-K | 85 |
| 79 | 1737.1 | G-N-L-K-N-G-V-N-D-I-K-N-H-K-W | 86 |
| 80 | 1542.8 | N-G-V-N-D-I-K-N-H-K-W-F-A | 87 |
| 81 | 1875.1 | V-N-D-I-K-N-H-K-W-F-A-T-T-D-W | 88 |
| 82 | 1894.3 | K-N-H-K-W-F-A-T-T-D-W-I-A-I-Y | 89 |
| 83 | 1898.3 | W-F-A-T-T-D-W-I-A-I-Y-Q-R-K-V | 90 |
| 84 | 1837.2 | T-D-W-I-A-I-Y-Q-R-K-V-E-A-P-F | 91 |
| 85 | 1807.3 | A-I-Y-Q-R-K-V-E-A-P-F-I-P-K-F | 92 |
| 86 | 1459.9 | R-K-V-E-A-P-F-I-P-K-F-K | 93 |
| 87 | 1630.1 | K-V-E-A-P-F-I-P-K-F-K-G-P-G-D | 94 |

TABLE 1-continued

| Peptide | Molecular Weight | Sequence | SEQ ID NO: |
|---|---|---|---|
| 88 | 1652.1 | P-F-I-P-K-F-K-G-P-G-D-T-S-N-F | 95 |
| 89 | 1590.9 | K-F-K-G-P-G-D-T-S-N-F-D-D-Y | 96 |
| 90 | 1816.9 | G-P-G-D-T-S-N-F-D-D-Y-E-E-E-I | 97 |
| 91 | 1845 | S-N-F-D-D-Y-E-E-E-I-R-V-S-I | 98 |
| 92 | 1752.9 | D-Y-E-E-E-I-R-V-S-I-N-E-K | 99 |
| 93 | 1633.9 | E-E-E-I-R-V-S-I-N-E-K-C-G-K | 100 |
| 94 | 1886.3 | I-R-V-S-I-N-E-K-C-G-K-E-F-S-E-F | 101 |
| 95 | 1764 | E-D-F-L-K-K-W-E-S-P-A-Q-N-T-A | 102 |
| 96 | 1509.7 | K-K-W-E-S-P-A-Q-N-T-A-H-L | 103 |

One letter codes used herein include: A, Alanine; R, Arginine; N, Asparagine; D, Aspartate; C, Cysteine; E, Glutamate; Q, Glutamine; G, Glycine; H, Histidine; I, Isoleucine; L, Leucine; K, Lysine; M, Methionine; F, Phenylalanine; P, Proline; S, Serine; T, Threonine; W, Tryptophan; Y, Tyrosine; and V, Valine.

Unexpectedly, individual peptides in the library exhibited significant inhibitory effects toward AKT. These peptides included peptide 49 (SEQ ID NO:56), 53 (SEQ ID NO:60), 62 (SEQ ID NO:69), 63 (SEQ ID NO:70) and 64 (SEQ ID NO:71). Combinations of consecutive overlapping peptide fragments were also assayed for an effect on the catalytic activity of AKT. A significant inhibitory effect was also observed when peptides 25 through 36 were combined (i.e., SEQ ID NOs:32-43), peptides 37 through 48 were combined (i.e., SEQ ID NOs:44-55), peptides 49 through 60 were combined (i.e., SEQ ID NOs:56-67), and peptides 61 through 72 were combined (i.e., SEQ ID NOs:68-79).

Of particular interest with regard to inhibitory activity toward AKT was peptide Ala-Lys-Arg-Val-Lys-Gly-Arg-Thr-Trp-Thr-Leu-Cys-Gly-Thr-Pro-Glu-Tyr (SEQ ID NO:60) which flanked the Thr-197 phosphorylation site of PKAc. This peptide, designated ZaTa, was sufficient to potently inhibit the in vitro catalytic activity of AKT. The phosphorylation level of Ser-9 GSK-3 GST substrate was significantly reduced after adding the ZaTa peptide to the AKT1 kinase assay as determined by separating the in vitro kinase assay products by SDS-PAGE and western blot analysis with a phospho-specific antibody which specifically recognizes phosphorylated GSK-3☐ at Ser-9. Furthermore, the inhibitory effect of ZaTa peptide was compared with an adjacent peptide (Gly-Phe-Ala-Lys-Arg-Val-Lys-Gly-Arg-Thr-Trp-Thr-Leu; SEQ ID NO:59), a peptide that overlaps with the 11 N-terminal amino acid residues of the ZaTa peptide and carries the Thr-197 phosphorylation site. In this assay, the level of incorporation of $-^{32}$P into Ser-21 GSK-3☐ substrate peptide was used as the measure of AKT1 in vitro catalytic activity. While the adjacent overlapping peptide was not able to inhibit AKT1, ZaTa peptide potently inhibited AKT1 catalytic activity in vitro (IC-50 ~0.1 µM; FIG. 1). ZaTa peptide itself was not a substrate for AKT, as determined by control kinase reactions that contained this peptide and AKT only. This indicated that phosphorylation at Thr-197 by AKT itself was not required for the inhibition of AKT by PKAc and the amino acid sequence, biochemical characteristics and/or structure flanking the Thr-197 site plays a role in inhibiting AKT. ZaTa peptide, which is derived from the native inhibitor of AKT, i.e., PKAc, potently inhibited AKT and in an independent series of kinase assays did not exhibit any inhibitory effect on the catalytic activity of PKAc, which, like AKT, is a member of the AGC family of kinases.

Similar to its in vitro inhibitory activity, the ZaTa peptide fragment was also able to potently and efficiently inhibit AKT in the brain. After the stereotactic injection of ZaTa peptide, a decrease in the phosphorylation level of AKT substrates in the striatum of a brain hemisphere was observed as compared to the other hemisphere that was injected with DMSO as the vehicle. These in vivo immunofluorescence results were also confirmed by western blot analyses, which showed a significant decrease in the phosphorylation level of AKT substrates in vivo one hour after the stereotactic injection of ZaTa peptide. As a specific substrate, the phosphorylation level of GSK-3☐ at Ser-9 was also evaluated. A specific reduction of the phosphorylation level of GSK-3☐ at Ser-9 was observed after the stereotactic injection of the ZaTa peptide into the striatum of one hemisphere, compared to the other hemisphere injected with DMSO as the vehicle. The decrease was specific to the AKT phosphorylation site on GSK-3☐ at Ser-9, since a change in the phosphorylation level of GSK-3☐ at Tyr-216 or GSK-3☐ at Tyr-279 was not observed. Moreover, the in vivo reduction of the phosphorylation of AKT substrates was more obvious at the injection site, since a significant change in the phosphorylation of AKT substrates in the frontal cortex or cerebellum between the two hemispheres was not observed. These data not only confirmed the inhibitory effect of ZaTa peptide on the AKT catalytic activity in vivo, but also demonstrated the efficient distribution and absorption of the ZaTa peptide throughout brain tissue. To test the specificity/selectivity of ZaTa as the inhibitor of AKT1 versus the other major kinases, a series of in vitro kinase assays was performed at $IC_{50}$ for AKT1 and at ten times higher concentrations. A panel of the following 32 kinases was first tested in vitro using the active form of each kinase and a specific substrate: AKT2, AKT3, PKA, PKC☐, PKC, PI3K☐, PI3K☐, PI3K, SGK, PAK2, PAK3, SAPK2/p38, Abl, CaMKII, CDK1/cyclinB, CDK5/p35, CK1, CK2, CSK, GSK3☐, GSK3☐, JNK1☐1, MAPK1, p70S6K, PDGFR☐, PDGFR☐, PDK1, PKG1☐, TrkB, JAK2, JAK3, and Syk. At $IC_{50}$ for AKT1 (0.1 µM), ZaTa showed no significant inhibition on any of the above kinases in vitro. However, at ten times higher concentration, ZaTa inhibited AKT2 (63%), PI3K☐ (72%), p70S6K (64%), SGK (73%), PAK3 (83%), JAK3

(79%), TrkB (84%), and Abl (42%). To confirm the in vitro inhibitory effect on these kinases in cells, a cell-based assay was used to determine the effect of labeled ZaTa on the phosphorylation levels of well-known intracellular substrates for each kinase (Zipfel, et al. (2004) Curr. Biol. 14:1222-1231; Wang, et al. (2003) Arch. Biochem. Biophys. 410:7-15; King, et al. (1998) Nature 396:180-183; Rangone, et al. (2004) Eur. J. Neurosci. 19:273-279; Middlemas, et al. (1994) J. Biol. Chem. 269:5458-5466; Huang, et al. (1999) J. Biol. Chem. 274:7870-7878). The results of this cell-based kinase assay confirmed that ZaTa could inhibit p70S6K besides AKT. In contrast, intracellular entry of labeled ZaTa did not cause inhibition of PI3K, SGK, PAK3, JAK3, TrkB or Abl, the kinases that ZaTa could inhibit at higher concentrations in vitro. These data showed that ZaTa had a selective inhibitory effect on AKT1 at nanomolar concentrations. However, at micromolar concentrations ZaTa can also inhibit other select kinases, in particular p70s6K in cell-based assays. Given that most of the above-listed kinases have no known inhibitor, it is contemplated that the ZaTa could be used at micromolar concentrations in in vitro studies to inhibit the activity of the select kinases.

To analyze in vivo selectivity, ZaTa was injected into one hemisphere and DMSO in the other hemisphere, as above, and a series of western blot analyses was preformed with phospho-specific antibodies which recognize a phosphorylated substrate or each one of the kinases that ZaTa inhibited at higher concentrations in vitro. The results of this analysis confirmed potent in vivo inhibition of p70S6K by ZaTa, and a weaker in vivo inhibition of Abl. No in vivo inhibitory effects were observed for the other kinases assayed. Given the high functional and structural homology between p70S6K and AKT, the in vivo inhibitory effect of ZaTa on p70S6K was contemplated. Furthermore, the in vivo effect of ZaTa on the phosphorylation levels of substrates for PKA, PKC, CDKs using phospho-specific antibodies recognizing the phosphorylated consensus sites of these kinases was analyzed. In contrast to the consistent decrease in phosphorylation of AKT substrates, significant changes in the phosphorylation level of PKA, PKC and CDKs substrates was not observed after in vivo injection of ZaTa.

As a striatal specific substrate for PKA and CDK5, the phosphorylation level of DARPP-32 was determined at Thr-34 (the PKA site) or at Thr-75 (the CDK5 site)(Huang, et al. (1999) supra). ZaTa did not cause any significant change in the phosphorylation of DARPP-32 at either of these sites. Therefore, compared to the other major family of kinases expressed in the brain, (i.e., PKA, PKC and CDKs), the ZaTa peptide fragment selectively inhibited AKT in vivo.

Peptides can be very effective inhibitors since they efficiently bind to and inhibit enzymatic activity. However, intracellular delivery of peptides can limit their use. With the exception of a few peptides known as cell-penetrating peptides (CPPs), which have been recognized for their use in site-specific drug delivery, inhibitory peptides can have limited intracellular accumulation in in vivo enzymatic studies. CPP neuropeptides function as neurotransmitters in central and peripheral nervous systems. Based on the primary structure of the ZaTa peptide (i.e., a peptide having a basic arm of several basic residues at the N-terminus and a polar arm composed of several residues with free hydroxyl group at the C-terminus) and in vivo inhibitory effect in the brain, it was determined whether ZaTa peptide was a CPP. The ZaTa peptide was labeled with a red fluorescent dye at its N-terminus given that its C-terminus was important for inhibitory activity. The efficiency of the labeling and the purity of the labeled peptide were assessed by mass spectrometry.

The ZaTa peptide was found to penetrate into cells and co-localize with AKT thereby demonstrating that AKT is an intracellular target for ZaTa peptide. The cellular pattern of localization of ZaTa peptide varied from cell to cell; some cells showed strong nuclear signals, some showed a cytoplasmic pattern of staining with aggregates, and some showed a bright signal on the cell membrane. These different localization patterns of ZaTa within the cell were usually accompanied with redistribution of AKT to the site of ZaTa. In addition to the cellular redistribution of AKT upon entry of ZaTa, there was also a decrease in the phosphorylation level of AKT substrates in these cells. Similar results were obtained in vivo after stereotactic injection of fluorescent ZaTa into the frontal cortex, wherein a specific reduction in phosphorylation level of AKT substrates was observed in cells that were positive for ZaTa. These in vitro and in vivo observations showed that ZaTa not only co-localized with AKT inside the cell but also inhibited its catalytic activity.

Entry of ZaTa into the cell also caused different patterns of expression of PKAc, depending on the localization of ZaTa. For example, there was a significant decrease in PKAc immunoreactivity in cells displaying a strong nuclear signal for ZaTa, whereas cells with cytoplasmic aggregates of ZaTa generally showed an increase in PKAc protein levels. These data indicate that the proper activity of AKT in the cell can influence the expression of PKAc. Not wishing to be bound by theory, it is believed that nuclear redistribution of AKT, due to treatment with ZaTa, caused transcriptional changes that suppressed the expression of PKAc. Alternatively, redistribution of ZaTa within cytoplasmic compartments could have caused a compensatory effect, i.e., upregulation of PKAc, to compensate for the decrease in activity of AKT.

The phenotypic consequence of disrupting the AKT-PKAc complex was also determined. ZaTa peptide was injected into the striatum of one hemisphere of the brain and DMSO, as vehicle, was injected into the other brain hemisphere of an adult C57BL/6 mouse under anesthesia. The brain was removed and dissected. Equal protein amounts from each hemisphere were subjected to immunoprecipitation by an anti-AKT antibody. The amount of AKT protein immunoprecipitated from the right (vehicle-treated) and left (ZaTa-treated) striatum were comparable; however, the amount of PKAc in physical contact with AKT was dramatically reduced after treatment with ZaTa. This showed that ZaTa could disrupt the physical complex between AKT and PKAc in vivo. To compare PKAc protein levels in the ZaTa- and vehicle-treated brain hemisphere lysates, western blot analysis was conducted. Although there were comparable amounts of PKAc in both hemispheres, a clear increase in molecular weight was observed for PKAc in the hemisphere treated with ZaTa. This indicates that treatment with ZaTa caused an electro-mobility change in PKAc, possibly due to post-translational changes in PKAc molecules.

Figure 2:
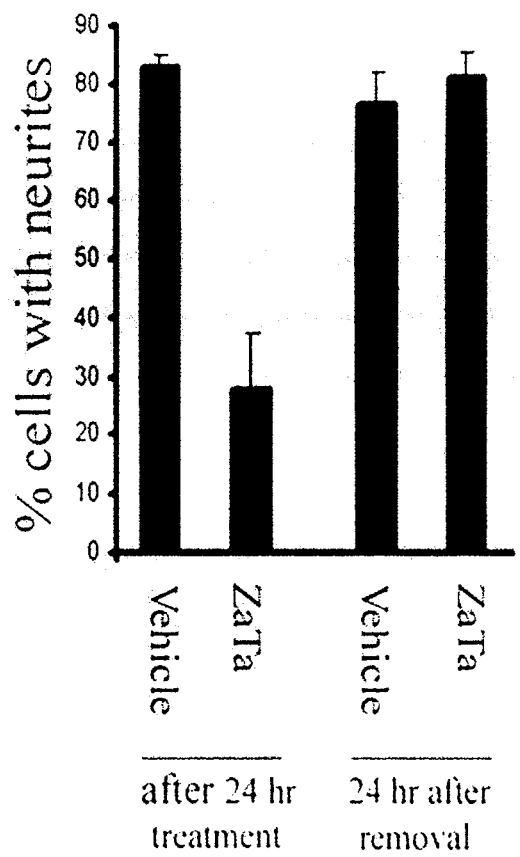
FIG. 2 shows the percent of individual neurons with neuronal cell processes 24 hours after treatment with ZaTa (left bars) or 24 hours after treatment with ZaTa followed by a 24-hour incubation in the absence of ZaTa (right bars).

As disclosed herein, N2a cells showed a neurite-specific pattern of AKT-PKAc interaction on their neuronal cell processes. Accordingly, the stability and phenotypic consequences of the AKT-PKAc complex was also analyzed in cultured neurons. N2a cells were treated with vehicle, ZaTa or control peptide for 24 hours. Media was removed after the 24-hour treatment and an equal number of cells from each treatment group was either cultured for another 24 hours without treatment, or lysed and subjected to immunoprecipitation with an antibody against AKT. Those cells cultured for another 24 hours were also harvested and subjected to immunoprecipitation. In parallel, the number of individual neurons with neurites was counted. Treatment with ZaTa reduced the amount of PKAc in physical contact with AKT, an effect which was reversible by a 24-hour incubation in the absence of ZaTa. Concurrently, cells treated with ZaTa exhibited a significant reduction in the number of neurons with neurites (FIG. 2), an effect which was reversible by a 24-hour incubation in the absence of ZaTa. These data not only confirmed the in vivo observations showing the disruption of AKT-PKAc complex by ZaTa, but also showed the correlation of neurite formation with the amount of PKAc in physical contact with AKT in cultured neurons. Moreover, these data indicate that the effect of ZaTa is reversible. Live images of N2a neurons were captured following treatment with vehicle or ZaTa (2 or 5 µM). These images showed the normal pattern of neurite morphology in untreated N2a cells, wherein treatment of N2a cells with ZaTa peptide caused dramatic morphological changes, in a dose-dependent manner. ZaTa-mediated changes included a progressive loss of neurites, inhibition of new neurite formation, loss of cell motility, as well as formation of large cell colonies.

To determine the phenotypic effect of disrupting the AKT-PKAc complex in an in vivo setting, ZaTa peptide was stereotactically injected into the brain of a mouse and the animal was perfused 18 hours after recovery from surgery. Because AKT is known to have a role in axonal morphology (Markus, et al. (2002) Neuron 35:65-76), coronal sections of striatum were stained with neurofilament-H(NF—H), as an axonal-specific marker. Changes in the staining pattern of axonal filament bundles in striatum were observed upon stereotactic injection of ZaTa peptide, as compared to the other brain hemisphere injected with DMSO as vehicle. To rule out the effect of tissue damage and show that striatal tissue structure was maintained following surgery, sections were co-labeled with a nuclear marker (Draq5). NF—H and nuclear marker staining of the same Z step showed similar tissue structure in both vehicle- and ZaTa-treated hemispheres of the same coronal section. These data, consistent with the co-localization observations disclosed herein, indicate a role for AKT in axon growth and the acceleration of axonal regeneration (see also Markus, et al. (2002) supra; Namikawa, et al. (2000) J. Neurosci. 20:2875-2886). PKA is also known to have a role in regeneration of growth cones on axons (Chierzi, et al. (2005) Eur. J. Neurosci. 21:2051-2062). Therefore, given the data provided herein, it is believed that a proper interaction between AKT and PKAc is involved in maintaining normal neuronal morphology.

AKT affects a network that positively regulates G1/S cell cycle progression through several mechanisms that involve the expression and subcellular localization of the CDK inhibitor p27$^{Kip1}$ (Blain and Massague (2002) Nat. Med. 8:1076-1078; Liang, et al. (2002) supra; Shin, et al. (2002) supra; Viglietto, et al. (2002) supra). Based on these studies, the effect of ZaTa peptide on cell proliferation was assessed. Using an MTT-based proliferation assay, a dose-dependent decrease in the number of live cells was observed. Western blot analysis showed a concomitant decrease in the phosphorylation level of AKT substrates in N2a cells after treatment with different doses of ZaTa peptide. Capturing live images of cultured N2a cells in the presence of different concentrations of the ZaTa peptide confirmed an obvious reduction in the number of dividing cells. Thus, consistent with the previous reports showing a positive role of AKT in cell cycle progression, the data disclosed herein demonstrate the inhibitory role of the ZaTa peptide in the rate of cell proliferation.

Figure 3:
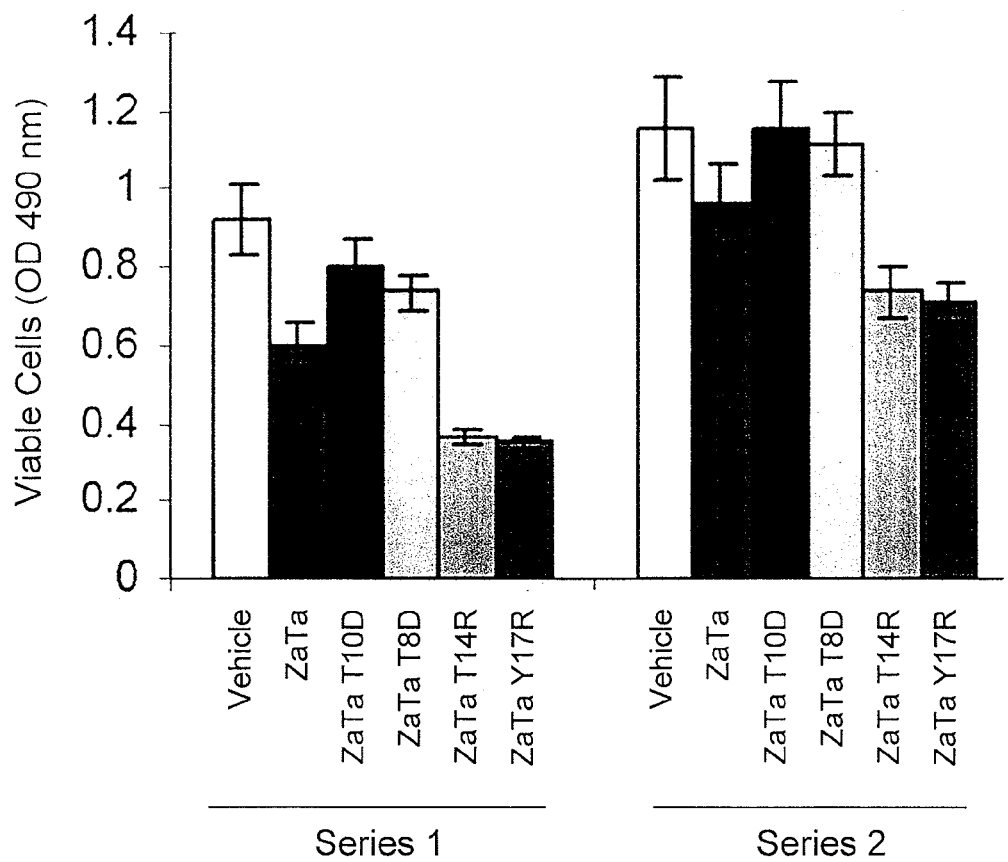
FIG. 3 shows the number of viable N2a cells after treatment with ZaTa and ZaTa variants based on the experiment of Example 4. Histogram series 1 shows results of an MTT assay of cells after a 48-hour treatment with 10 μM with ZaTa or ZaTa variants. In histogram series 2, treatments were removed after 24 hours and cells were incubated for another 24 hours without treatment. Control assays on another plate treated for 24 hours showed smaller but similar changes as shown in histogram series 1. Mitochondrial activity (reflecting cellular growth and viability) in the presence of ZaTa and ZaTa variants (ZaTa T10D, ZaTa T8D, ZaTa T14R, and ZaTa Y17T) was evaluated by measuring the optical density ("OD") at 490 nm on a plate reader. ZaTa T10D refers to a ZaTa polypeptide variant in which the Threonine (T) at position 10 of SEQ ID NO: 60 is substituted by an Aspartic Acid (D). ZaTa T8D refers to a ZaTa polypeptide variant in which the Threonine (T) at position 8 of SEQ ID NO: 60 is substituted by an Aspartic Acid (D). ZaTa T14R refers to a ZaTa polypeptide variant in which the Threonine (T) at position 14 of SEQ ID NO: 60 is substituted by an Arginine (R). ZaTa Y17T refers to a ZaTa polypeptide variant in which the Tyrosine (Y) at position 17 of SEQ ID NO: 60 is substituted by an Threonine (T).

Based on the importance of the C-terminal arm of ZaTa for its inhibitory action on AKT, it was determined whether the free hydroxyl groups on residues Thr-8, Thr-10 (equivalent to Thr-197 in full-length PKAc), Thr-14 and Tyr-17 were important for the biological activity of this peptide. Mutants of ZaTa peptide were synthesized by replacing Thr-8 or Thr-10 residues with Asp (ZaTa$^{T8D}$ and ZaTa$^{T10D}$, respectively) as an amino acid with a negatively charged side chain. Mutants of ZaTa with the hydrophilic positively charged amino acid Arg at either position Thr-14 or Tyr-17 (ZaTa$^{T14R}$ and ZaTa$^{Y17R}$, respectively) were also synthesized. Replacing either Thr-8 or Thr-10 with an Asp significantly diminished the inhibitory effect of ZaTa on cell proliferation, while replacing Thr-14 or Tyr-17 with an Arg considerably augmented ZaTa activity (FIG. 3, histogram series 1). The inhibitory effect of ZaTa peptide on cell proliferation was reversible, to a large extent, after the removal of ZaTa treatment (FIG. 3, histogram series 2). While wild-type ZaTa caused a significant decrease in the number of live cells with doses as low as 2 µM, no significant differences in the number of live cells were observed 24 hours after removal of 10 µM wild-type ZaTa or DMSO vehicle. These observations showed that the biochemical properties of the side chain of the amino acids composing the primary structure of ZaTa peptide were important for the biological effects of this peptide. It is possible that ZaTa, like other peptides, can switch between the alpha/beta secondary structures, with one structure more favorable for its active conformation while the other one creates an inactive form. Therefore, the mutation of Thr-14 or Thr-17 to an Arg appeared to stabilize the structure of ZaTa to its active conformation while changing Thr-8 or Thr-10 to Asp was more favorable for generation of an inactive conformation.

Some cell proliferation assays, such as MTT, do not distinguish whether a decrease in the number of viable cells is due to a decrease in the number of dividing cells, or is a result of cell toxicity and death. Therefore, in addition to capturing live images, cells were stained with trypan blue at different time intervals following treatment with ZaTa and counted by a light microscope using a hemocytometer. The same dose-dependent decrease in the number of live cells was observed. However, although a significant increase in the number of dead cells was not seen after treatment with wild-type ZaTa, ZaTa$^{T8D}$, or ZaTa$^{T10D}$, counted at different time points from 12 to 72 hours, a significant increase in the number of dead cells was observed after treatment with ZaTa$^{T14R}$ or ZaTa$^{Y17R}$ only after 72 hours. This observation indicated that while the inhibitory effect of the wild-type ZaTa on AKT was reversible, the ZaTa$^{T14R}$ or ZaTa$^{Y17R}$ mutants could, by causing an irreversible inhibition of AKT, cause permanent changes leading to apoptosis and cell death. Alternatively, it was possible that the free hydroxyl group on Thr-14 or Tyr-17 created an unstable/cleavable binding of ZaTa with AKT, while the Arg-14 or Arg-17 made this binding more stable and non-cleavable.

The interaction between PKAc and AKT at the transcriptional level was also evaluated by decreasing PKAc alpha protein levels by RNA interference. Reduced PKAc levels resulted in an increase in the amount of AKT1 protein in non-neuronal HeLa cells as well as in neuronal NG-108 cells. AKT expression was also analyzed in a PRKACA (PKAc alpha) knockout mouse. Since homozygous knockout mice of this strain do not survive to adulthood, AKT1 protein levels were measured in a heterozygous PKAc mouse, which expressed 50% of the PKAc protein compared to wild-type. Protein extracts from the frontal cortex of the heterozygous PKAc mouse showed an increase in the AKT1 protein level. These data showed that in addition to the physical interaction between AKT and PKA, which affected their activity levels directly, there were active transcriptional mechanisms involved that regulated the protein level as well.

It is now well-established that AKT protects against apoptosis through phosphorylation and inhibition of pro-apoptotic mediators such as BAD, FOXO family members and IKK-☐ (Datta, et al. (1999) *Genes Dev.* 13:2905-2927). To demonstrate the effect of ZaTa on the protective function of AKT, non-proliferating neurons in primary cortical culture were analyzed as a model system that utilizes the minimal level of the cell proliferative activity of AKT. Primary neurons were treated with DMSO, 1 ☐M or 5 ☐M of either ZaTa or the control peptide for a duration of 1, 3, 16, 24, 48 or 72 hours. The number of apoptotic cells was counted following the TUNEL assay. The result of this experiment showed a marked dose-dependent increase in the number of TUNEL-positive cells after a 72-hour treatment with ZaTa as compared to the control peptide. The increase in the number of apoptotic neurons following treatment with ZaTa was consistent with its potent intra-neuronal inhibition of AKT.

To confirm the apoptotic inducing effect of ZaTa in vivo, ZaTa was delivered to the mouse brain via the nasal cavity, a minimally invasive procedure compared to the stereotactic surgery. Intranasal delivery of compounds into the brain is an efficient and effective way for local delivery of compounds, without the need for passing the blood brain barriers, the major obstacle for studying the effect of different inhibitors/activators in CNS (Vyas, et al. (2005) *Curr. Drug Deliv.* 2:165-175; Hrafnkelsdottir, et al. (2005) *Biol. Pharm. Bull.* 28:1038-1042). Repeated intranasal treatment of C57BL/6 mice with labeled ZaTa for three days significantly increased the number of apoptotic cells in the olfactory bulb, specifically in cells stained positive for ZaTa. This was visualized by double labeling of the brain sections with fluorescent TUNEL and a nuclear marker. By contrast, no change in the number of apoptotic cells was observed in cells which stained negative for ZaTa or following treatment with the control peptide. Taken together, these data indicate that ZaTa can inhibit AKT-dependent functions both in vitro and in vivo.

Accordingly, the present invention relates to PKAc compositions for use in methods of inhibiting AKT activity in the treatment of diseases or conditions associated with aberrant expression of AKT. PKAc compositions embraced by the present invention include pharmaceutical compositions containing the catalytic subunit of Protein Kinase A (PKAc), or a fragment or variant fragment thereof, in admixture with a pharmaceutically acceptable carrier. As combinations of PKAc fragments were also found to inhibit AKT activity, particular embodiments embrace pharmaceutical compositions containing one or more PKAc fragments (e.g., SEQ ID NOs:32-43, SEQ ID NOs:44-55, SEQ ID NOs:56-67, or SEQ ID NOs:68-79).

In accordance with the instant compositions, PKAc protein, or a fragment thereof, can be isolated from a variety of sources including, for example, human (e.g., GENBANK Accession No. NP_002721, SEQ ID NO:1; GENBANK Accession No. NP_997401, SEQ ID NO:2), bovine (e.g., GENBANK Accession No. CAA47627, SEQ ID NO:3), canine (e.g., GENBANK Accession No. NP_001003032, SEQ ID NO:4), mouse (e.g., GENBANK Accession No. NP_032880, SEQ ID NO:5), or rat (e.g., GENBANK Accession No. P27791, SEQ ID NO:6).

When employing a full-length (e.g., 340 to 350 amino acid residue protein) or near full-length PKAc protein (e.g., at least 300 amino acid residues of the full-length protein), particular embodiments embrace a PKAc protein with an amino acid sequence set forth herein as SEQ ID NO:7, said sequence being identified by alignment of human, bovine, canine, mouse, and rat PKAc proteins (FIG. 4).

In embodiments involving at least a fragment of PKAc, said fragment is desirably at least 5, 10, 15, 20, 30, 40, 50, 60, 70, 80, 90, or 100 consecutive amino acid residues of a PKAc of SEQ ID NO:7. Such fragments can be derived from a variety of locations within the PKAc protein sequence. In particular embodiments, the PKAc fragment has the amino acid sequence of SEQ ID NO:56, SEQ ID NO:60, SEQ ID NO:69, SEQ ID NO:70, or SEQ ID NO:71.

In particular embodiments, a PKAc fragment contains all or at least a portion (e.g., at least 5, 10, 15, or 20 amino acid residues) of the activation loop of PKAc. The activation loop of PKAc is identified herein as amino acid residues located at positions 185 to 209 of SEQ ID NO:7 (see FIG. 4). Exemplary fragments of PKAc containing a portion of the activation loop of PKAc are disclosed herein as SEQ ID NO:60 (i.e., ZaTa) and SEQ ID NO:56.

Variant fragments of PKAc are also embraced by the present invention. As used herein, a variant PKAc fragment is a fragment of PKAc which contains one or more amino acid substitutions in a wild-type PKAc fragment that enhance the inhibitory activity of a PKAc fragment toward AKT as compared to the wild-type PKAc fragment. For example, mutants of ZaTa containing a hydrophilic, positively charged amino acid residue at positions 14 and 17 (e.g., ZaTa$^{T14R}$ and ZaTa$^{T17R}$, respectively) were found to considerably augment ZaTa activity. Additional variant PKAc fragments can be generated by random or site-specific mutation of a wild-type PKAc fragment and identified based on inhibitory activity toward AKT. Moreover, variant PKAc fragments can be specifically designed to bind to and inhibit AKT activity. For example, a molecular docking program is used to identify key amino acid residues involved in the binding a PKAc protein or PKAc fragment to AKT. Subsequently, site-specific mutation of each PKAc amino acid residue identified as being involved in AKT binding is carried out and the resulting library is screened to identify variant PKAc fragments exhibiting inhibitory activity toward AKT.

Rational design of variant PKAc fragments is facilitated by the known crystal structure of an activated AKT in complex with GSK-3 peptide and AMP-PNP (Yang, et al. (2002) *Nat. Struct. Biol.* 9:940-944). The structure revealed the binding of GSK-3 peptide through the activation loop of AKT. The observation that the short sequence of ZaTa peptide (SEQ ID NO:60), surrounding the Thr-197 located in the activation loop of PKAc, was sufficient to inhibit AKT as potently as the full-length PKAc protein indicates that during the course of interaction between the active conformations of the two molecules, residues adjacent to the Thr-197 site are essential and sufficient for this inhibition. Not wishing to be bound by theory, it is believed that in the active conformation of full-length PKAc, a specific sequence surrounding Thr-197 docks into the active site of AKT thereby preventing efficient phosphorylation of Thr-308 and/or binding of GKS-3 substrate peptide to the activation loop of AKT and AKT fails to phosphorylate GSK-3 at Ser-9 site. Looking at the other component of this interaction, it is found that in contrast to the inhibitory effect of active PKAc, AKT phosphorylates PKAc at Thr-197 which increases its catalytic activity. The data disclosed herein indicate that this phosphorylation is not required for the inhibitory effect of PKAc toward AKT; however, it provides a conformational change that not only favors a more active state for PKAc, but also exposes residues surrounding this site for the subsequent inhibitory effect of full-length PKAc on AKT. Therefore, as a structural model, the PKAc/AKT interaction functions as a molecular on/off switch in which AKT phosphorylates Thr-197 of PKAc first, which results in a more active conformation for PKAc and its binding to the activation loop of AKT provides an inactive conformation for AKT. In an analysis of cAMP-induced activation of PKA, the crystal structure of the catalytic and regulatory (RI□) subunits of PKA in complex was determined (Kim, et al. (2005) *Science* 307:690-696). This analysis indicates that the PKA inhibitor peptide of the R1 subunit is sufficient to inhibit PKAc catalytic activity.

Accordingly, particular embodiments of the present invention embrace a 10 to 30 amino acid residue PKAc fragment or variant PKAc fragment of the structure $(Xaa_1)_n$-Thr-$(Xaa_2)_m$, wherein n and m are each independently 4 to 25 amino acid residues, each of $Xaa_1$ and $Xaa_2$ is independently any amino acid residue, and wherein at least four of $Xaa_1$ are basic amino acid residues and at least two of $Xaa_2$ are polar amino acid residues or hydrophilic positively charged amino acid residues. Other $Xaa_1$ and $Xaa_2$ amino acid residues which are not basic, polar or hydrophilic positively charged, can by any amino acid residue with apolar or polar characteristics, and in some embodiments, an acidic residue is present.

Basic amino acid residues are generally hydrophilic having a side chain exhibiting a pK value of greater than about 6 when the amino acid is included in a peptide or polypeptide. Basic amino acids typically have positively charged side chains at physiological pH due to association with hydronium ion. Basic amino acids include His (H), Arg (R) and Lys (K).

Polar amino acid residues are generally hydrophilic having a side chain that is uncharged at physiological pH, but which has at least one bond in which the pair of electrons shared in common by two atoms is held more closely by one of the atoms. Polar amino acids include Asn (N), Gln (Q), Ser (S) and Thr (T).

As used in the context of the present invention, a hydrophilic amino acid residue refers to an amino acid having a side chain exhibiting a hydrophobicity of less than zero according to the normalized consensus hydrophobicity scale of Eisenberg, et al. ((1984) *J. Mol. Biol.* 179:125-142). Hydrophilic amino acids include Thr (T), Ser (S), His (H), Glu (E), Asn (N), Gln (Q), Asp (D), Lys (K) and Arg (R), wherein hydrophilic amino acid residues which are positively charged include His, Lys and Arg.

Apolar amino acid residues are typically hydrophobic having a side chain that is uncharged at physiological pH and has a non-polar side chain. As used in the context of the present invention, apolar amino acids include L-Leu (L), L-Gly (G), L-Val (V), L-Ile (I), L-Met (M), Cys (C), Trp (W), Pro (P), and L-Ala (A).

Acidic amino acid residues are hydrophilic having a side chain exhibiting a pK value of less than about 6 when the amino acid is included in a peptide or polypeptide. Acidic amino acids typically have negatively charged side chains at physiological pH due to loss of a hydrogen ion. Acidic amino acids include Glu (E) and Asp (D).

In accordance with the present invention, exemplary peptides of the structure $(Xaa_1)_n$-Thr-$(Xaa_2)_m$ include, but are not limited to, Ala-Lys(basic)-Arg(basic)-Val-Lys(basic)-Gly-Arg(basic)-Thr-Trp-Thr-Leu-Cys-Gly-Thr(polar)-Pro-Glu-Tyr(polar) (SEQ ID NO:60) and Ala-Lys(basic)-Arg(basic)-Val-Lys(basic)-Gly-Arg(basic)-Thr-Trp-Thr-Leu-Cys-Gly-Arg(hydrophilic positive)-Pro-Glu-Arg(hydrophilic positive) (SEQ ID NO:104), wherein Thr-197 relative to the full-length PKAc protein is underlined.

As used herein, "synthesized" or "synthetic" PKAc proteins and fragments of the present invention encompasses polypeptides that are recombinantly produced, purified from a natural source, or chemically synthesized. For yield and ease in purification, it is conventional in the art to produce proteins and fragments thereof by recombinant protein methodologies. Methods for producing recombinant proteins in vivo (i.e., cell-based) generally include isolating a nucleic acid molecule encoding the protein or fragment of interest, incorporating the nucleic acid molecule into a recombinant expression vector in a form suitable for expression of the protein or fragment in a host cell, and expressing the protein. A suitable form for expression provides that the recombinant expression vector includes one or more regulatory sequences operatively-linked to the nucleic acid molecule encoding the protein or fragment of interest in a manner which allows for transcription of the nucleic acids into mRNA and translation of the mRNA into the protein. Regulatory sequences can include promoters, enhancers and other expression control elements (e.g., polyadenylation signals). Such regulatory sequences and vectors encoding the same are known to those skilled in the art and are described in Goeddel, Gene Expression Technology: Methods in Enzymology 185, Academic Press, San Diego, Calif. (1990). Suitable vectors for recombinant protein expression in mammalian, yeast, or prokaryotic systems are commercially available from such sources as STRATAGENE®, INVITROGEN™, Pharmacia and the like. Many of these vectors encode heterologous polypeptides, i.e. signal sequences for secretion and/or other polypeptide which will aid in the purification of the protein or fragment of interest. Preferably, the heterologous polypeptide has a specific cleavage site to remove the heterologous polypeptide from the protein of interest. Other useful heterologous polypeptides which can be fused to the protein of interest are those which increase expression or solubility of the fusion protein or aid in the purification of the fusion protein by acting as a ligand in affinity purification. Typical fusion expression vectors include pGEX (Amersham Biosciences, Piscataway, N.J.), pMAL (New England Biolabs, Beverly, Mass.) and pRIT5 (Pharmacia, Piscataway, N.J.), which fuse glutathione-S-transferase, maltose E binding protein, or protein A, respectively, to the protein of interest. It should be understood that the design of the expression vector may depend on such factors as the choice of the host cell to be transfected and/or the level of expression required.

Introduction of the recombinant expression vector into a host cell (e.g., of eukaryotic or prokaryotic origin) can be carried out using any conventional technique for transforming cells. Suitable methods for transforming host cells are found in Sambrook, et al. (Molecular Cloning: A Laboratory Manual, 3rd Edition, Cold Spring Harbor Laboratory Press (2000)) and other laboratory manuals. The number of host cells transformed with a nucleic acid molecule encoding a PKAc protein or fragment will depend, at least in part, upon the type of recombinant expression vector used and the type of transformation technique used. A recombinant protein or fragment can be expressed transiently, or more typically, stably expressed by integrating the recombinant expression vector into the genome of the host cell or by episomal maintenance of the vector.

Once produced, a PKAc protein or fragment can be recovered from culture medium as a secreted polypeptide, or alternatively recovered from host cell lysates when directly expressed without a secretory signal. When a PKAc protein or fragment is expressed in a recombinant host cell other than one of human origin, the PKAc protein or fragment is substantially free of proteins or polypeptides of human origin. However, it may be necessary to purify the PKAc protein or fragment from recombinant cell proteins or polypeptides using conventional protein purification methods to obtain preparations that are substantially homogeneous as to the PKAc protein or fragment. As a first step, the culture medium or lysate is centrifuged to remove particulate cell debris. The membrane and soluble protein fractions are then separated. The recombinant protein may then be purified from the soluble protein fraction. The recombinant protein thereafter is purified from contaminant soluble proteins and polypeptides using any of the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX™ G-75; and ligand affinity chromatography.

In addition to recombinant production, a PKAc protein or fragment can be produced by direct peptide synthesis using solid-phase techniques (Merrifield R. B. (1963) *J. Am. Chem. Soc.* 85:2149-2154). Protein synthesis can be performed using manual techniques or by automation. Automated synthesis can be achieved, for example, using APPLIED BIOSYSTEMS® 431A Peptide Synthesizer (Perkin Elmer, Boston, Mass.). When producing a full-length or near full-length PKAc protein, various portions of the PKAc protein can be chemically-synthesized separately and combined using chemical methods to produce a full-length molecule.

Whether recombinantly-produced or chemically-synthesized, a PKAc protein or fragment can be further modified for use. For example, an isolated PKAc protein or fragment can be phosphorylated, acetylated, methylated or a combination thereof using well-known methods in prior to its use in inhibiting AKT activity. Moreover, PKAc and PKAc fragment-based therapeutics can be attached to a scaffold.

In some embodiments, the amino acid residues in the PKAc protein or fragments of present invention are selected from any of the naturally-occurring amino acids. In other embodiments, one or more or synthetic non-encoded amino acids are used to replace one or more of the naturally-occurring amino acid residues. Certain commonly encountered non-encoded amino acids include, but are not limited to: peptide mimetics or analogs; beta or gamma amino acids; the D-enantiomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); homoleucine (hLeu); homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro); and the like. Additional non-encoded amino acids are well-known to those of skill in the art (see, e.g., the various amino acids provided in Fasman (1989) *CRC Practical Handbook of Biochemistry and Molecular Biology*, CRC Press, Boca Raton, Fla., at pp. 3-70 and the references cited therein). Further, amino acids of the invention can be in either the L- or D-configuration.

A PKAc protein, or PKAc fragment or variant PKAc fragment can be used as a purified preparation, or in certain embodiments, formulated into a pharmaceutical composition containing an effective amount of a PKAc peptide, or at least one PKAc fragment or variant PKAc fragment, to decrease the expression or activity of AKT. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. For example, sterile saline and phosphate-buffered saline at physiological pH can be used. Preservatives, stabilizers, dyes and even flavoring agents can be included in the pharmaceutical composition. For example, sodium benzoate, sorbic acid and esters of p-hydroxybenzoic acid can be added as preservatives. In addition, antioxidants and suspending agents can be used. Liposomes, such as those described in U.S. Pat. No. 5,422,120, WO 95/13796, WO 91/14445, or EP 524,968 B1, are also suitable carriers.

Depending on the intended use, a pharmaceutical composition of the invention can be administered by any suitable means, including parenteral injection (such as intraperitoneal, subcutaneous, intratumoral or intramuscular injection), orally or by topical application (e.g., transdermal or via a mucosal surface). By pharmaceutically acceptable formulation is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies, including CNS delivery of nucleic acid molecules include material described in Boado et al., 1998, J. Pharm. Sci., 87, 1308-1315; Tyler et al, 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. All these references are hereby incorporated herein by reference. ZaTa was delivered into the brain via intranasal injection; ZaTa peptide was dissolved in tetraglycol (Sigma) to 0.5 mM final concentration, and 5 μl of the solution was injected to each nasal cavity.

Because ZaTa is a cell penetrating peptide and distributes rapidly throughout the human tissue, it has the "unique" advantage of local delivery into the site of tumor. In one exemplary embodiment, the therapeutic peptides of the invention are injected directly into the site of the tumor through, for example, stereotactic surgery. However, one potential disadvantage of this technique is that local injections are not generally formulated for sustained release delivery.

Therefore, additional formulation/delivery devices are also contemplated that provide for and/or are adapted for controlled and/or sustained release of a therapeutic of the invention. For example, the therapeutic peptides of the invention can be conjugated (either covalently or via non-covalent bonds) or merely entrapped in a pharmaceutically acceptable (i.e., biologically inert or biologically compatible) and/or biologically absorbable carrier material, for example a polymer matrix, biopolymer matrix, and/or other matrix. As used herein, "biologically inert or biologically compatible" refers to materials that do not result in a significant allergic or immunogenic reaction in the host. In one embodiment, the material is comprised of collagen. Other materials include proteins, like elastin, saccharides and gels, and/or sols comprising saccharides, for example, hydroxypropyl cellulose (HPC), HPMC, methacrylates, and the like. In an exemplary embodiment, the material is an absorbable collagen sponge (ACS) or cross-linked collagen matrix, which is adapted to allow controlled and/or sustained release of the peptide into the tissue. The peptide could be inserted into a device or preshaped/prefabricated matrix material either contemporaneously or after formation of the delivery device. In still other embodiments the therapeutic peptide/biocompatible material (e.g., collagen) could be inserted into another device, which is also bioabsorbable and/or implantable, the device to be delivered into the tumor site to allow sustained local delivery. The combination of therapeutic peptide/biocompatible material could also be inserted through a different external device. See, McKay, B. Local Sustained Delivery of Recombinant Human Bone Morphogenetic Protein-2 (rhHBMP-2). 31$^{st}$ Annual International Conference of the IEEE EMBS, Sep. 2-6, 2009; and Chan, B. P. Effects of Photochemical Cross-linking on the Microstructure of Collagen and a Feasability Study on Controlled Protein Release. Acta Biomaterialia, 4:1627-36 (2008), which are hereby incorporated by reference in their entirety.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Nucleic acid molecules of the invention can also be administered in the form of suppositories, e.g., for rectal administration of the drug or via a catheter directly to the bladder itself. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The amount of active ingredient that can be combined with the carrier materials to produce a single dosage form varies depending upon the host treated and the particular mode of administration. Dosage unit forms generally contain between from about 1 mg to about 1000 mg of an active ingredient.

It is understood that the specific dose level for any particular patient or subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The composition can also be administered to a subject in combination with other therapeutic compounds to increase the overall therapeutic effect. The use of multiple compounds to treat an indication can increase the beneficial effects while reducing the presence of side effects.

In another embodiment, an isolated nucleic acid molecule of the invention comprises a nucleic acid molecule that is a complement of the nucleotide sequence PKAc, a PKAc fragment or variant PKAc fragment. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect.

In certain embodiments, the invention encompasses host cells that have been modified to carry an exogenous or heterologous nucleic acid comprising a nucleic acid encoding for a PKAc protein, PKAc fragment or variant fragment thereof.

The term "host cell" includes a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

Derivatives or variants of the nucleic acids, proteins or peptides of the invention include, but are not limited to, molecules comprising regions that are substantially homologous to the nucleic acids or proteins of the invention, in various embodiments, by at least about 30%, 40%, 50%, 60%, 70%, 80%, 90%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Peptide and polypeptide modifications include phosphorylation, acetylation, and methylation. Nucleic acid derivatives and modifications include those obtained by gene replacement, site-specific mutation, deletion, insertion, recombination, repair, shuffling, endonuclease digestion, PCR, subcloning, and related techniques.

Furthermore, one of ordinary skill will recognize that "conservative mutations" also include the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS IN MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990) C&EN 36-47.

In yet another embodiment, a nucleic acid of the invention is expressed in mammalian cells using a mammalian expression vector. For suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

A polynucleotide can be a DNA molecule, a cDNA molecule, genomic DNA molecule, or an RNA molecule. A polynucleotide as DNA or RNA can include a sequence wherein T (thymidine) can also be U (uracil). If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process.

Transformation of a host cell with recombinant DNA may be carried out by conventional techniques as are well known to those skilled in the art. By "transformation" is meant a permanent or transient genetic change induced in a cell following incorporation of new DNA (i.e., DNA exogenous to the cell).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

In any of the embodiments, the nucleic acids encoding a PKAc protein, or PKAc fragment or variant PKAc fragments can be present as: one or more naked DNAs; one or more nucleic acids disposed in an appropriate expression vector and maintained episomally; one or more nucleic acids incorporated into the host cell's genome; a modified version of an endogenous gene encoding the components of the complex; one or more nucleic acids in combination with one or more regulatory nucleic acid sequences; or combinations thereof. The nucleic acid may optionally comprise a linker peptide or fusion protein component, for example, His-Tag, FLAG-Tag, fluorescent protein, GST, TAT, an antibody portion, a signal peptide, and the like, at the 5' end, the 3' end, or at any location within the ORF.

Where the host is prokaryotic, such as E. coli, competent cells which are capable of DNA uptake can be prepared from cells harvested after exponential growth phase and subsequently treated by the $CaCl_2$ method by procedures well known in the art. Alternatively, $MgCl_2$, RbCl, liposome, or liposome-protein conjugate can be used. Transformation can also be performed after forming a protoplast of the host cell or by electroporation. These examples are not limiting on the present invention; numerous techniques exist for transfecting host cells that are well known by those of skill in the art and which are contemplated as being within the scope of the present invention.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. The eukaryotic cell may be a yeast cell (e.g., Saccharomyces cerevisiae) or may be a mammalian cell, including a human cell. For long-term, high-yield production of recombinant proteins, stable expression is preferred.

As exemplified herein, a PKAc protein, or PKAc fragment or variant PKAc fragment, finds application in inhibiting the expression or activity of AKT (e.g., as determined by phosphorylation of the Ser-21 GSK-3 substrate peptide), wherein AKT inhibition results in a decrease in cell proliferation and a progressive dose-dependent loss of the existing neurites, as well as the inhibition of new neurite formation. Accordingly, not only does the present invention embrace the use of a PKAc protein, or a PKAc fragment or variant PKAc fragment, for decreasing proliferation of a cell, this invention provides methods for preventing or treating cancer or a neurodegenerative or psychiatric disease or condition.

AKT-mediated control of cell cycle progression is well-established in the art (see, e.g., Brazil, et al. (2004) supra). AKT regulates the cell cycle by facilitating G1/S transition and the initiation of M phase (Collado, et al. (2000) J. Biol. Chem. 275:21960-21968; Datta, et al. (1999) Genes Dev. 13:2905-2927; Franke, et al. (1997) Cell 88:435-437). AKT also phosphorylates MDM2 which causes its translocation to the nucleus, where it promotes the degradation of p53, leading to a reduction in the transcription of $p21^{Cip1}$ mRNA. In the nucleus, FOXO transcription factors increase the transcription of $p27^{Kip1}$, but this function is inhibited by AKT phosphorylation, which causes FOXO proteins to remain in the cytoplasm. The cyclin-dependent kinase (CDK) inhibitor $p21^{Cip1}$ and $p27^{Kip1}$ proteins can also be phosphorylated by AKT, leading to their accumulation in the cytoplasm, which relieves the inhibition of CDK2 activity and facilitates G1/S transition (Blain and Massague (2002) supra; Liang, et al. (2002) supra; Shin, et al. (2002) supra; Viglietto, et al. (2002) supra). AKT also drives the cell cycle to M phase by phosphorylating a checkpoint protein with FHA and ring finger domains (CHFR) and Myt1 (Brazil, et al. (2004) supra; Okumura, et al. (2002) supra). In view of the fact that AKT plays an important role in regulation of multiple checkpoints during the cell cycle, and hyperactivity of AKT is known to be involved in the most prevalent human malignancies including breast cancer, prostate cancer, lung cancer, gastrointestinal tumors, pancreatic cancer, hepatocellular carcinoma, thyroid cancer and CNS malignancies (such as glioblastoma and gliomas), PKAc and fragments thereof (e.g., ZaTa peptide) can be used for inhibiting cancer cell proliferation, e.g., in the prevention and treatment of cancer.

Glioblastoma is the most common primary central nervous system tumor in adults. Mitotic activity in glioblastoma is abundant, and vascular endothelial proliferation is prominent. Both of these two mechanisms are tightly regulated by AKT through phosphorylation and protein-protein interaction (Brazil, et al. (2002) supra). These features cause a rapid growth rate and most patients die within one year of diagnosis (Underwood (2004) General and systemic pathology. 4$^{th}$ Edition). AKT signaling pathway is implicated in tumor initiation and maintenance of glioblastoma and gliomas (Lefranc, et al. (2005) J. Clin. Oncol. 23:2411-22; Kesari, et al. (2005) Curr. Neurol. Neurosci. Rep. 5:186-97) and targeting AKT is an effective strategy for treating of brain tumors (Kesari, et al. (2005) supra). Inhibitors of AKT have been investigated in clinical trials for treatment of glioblastoma (Carpentier (2005) *Bull. Cancer* 92:355-9). The effect of monoclonal antibodies and small peptidic hormones for local targeting of malignant gliomas has been investigated (Merlo, et al. (2003) *Acta Neurochir. Suppl.* 88:83-91) with significant tumor uptake by small peptidic hormone receptors.

The exemplary ZaTa peptide disclosed herein was found to be effectively absorbed and distributed throughout mouse brain tissue and specifically inhibit AKT following local administration of a very small dose of this peptide (only 1 μL of mM solution). ZaTa peptide also potently inhibited cell proliferation of neuronal cells derived from malignant neuroblastoma cell line (N2a cells). Considering the combination of the three effects of ZaTa peptide, i.e., distribution in brain tissue, inhibition of AKT in vivo, and inhibition of cell proliferation, ZaTa peptide and variant PKAc fragments will be useful in treatment of human CNS tumors, in which these three processes have been shown to play an important role in pathology development and poor prognosis. In treatment of CNS tumors, a PKAc fragment such as ZaTa peptide has the advantage of being delivered directly into the tumor site using advanced and minimally invasive neurosurgical techniques. Current treatments of CNS tumors usually involve either invasive neurosurgery with potential serious post-surgical complications or intensive radiotherapy.

Activation of the AKT pathway has also been demonstrated to contribute to the pathogenesis of prostate cancer (Culig, et al. (2005) *Endocr. Relat. Cancer* 12:229-44), and inhibition of this signaling pathway is known to have therapeutic implications in human prostate adenocarcinoma (Wang, et al. (2004) *Neuron* 38:915-928). Therefore, targeting AKT with PKAc or a fragment thereof can be used in treatment of prostate cancer as well.

AKT is also documented as being involved in breast cancer. While peptide-based vaccines are commonly used for targeting breast cancer (Disis, et al. (2004) *Breast Dis.* 20:3-11), PKAc or fragments thereof can be used as primary or adjunct therapeutic agents in the treatment of breast cancer.

A method for inhibiting cell proliferation generally involves the step of contacting a cell (e.g., a cancer cell) with an effective amount of a PKAc, or a fragment or variant fragment thereof (e.g., in a pharmaceutical composition), thereby reducing the proliferation of the cell as compared to a cell not contacted with the PKAc, or PKAc fragment or variant PKAc fragment. Means for monitoring the reduction of cell proliferation are disclosed herein.

In the context of cancer cell proliferation and cancer prevention or treatment, an effective amount is considered an amount that decreases or inhibits cancer cell proliferation such that tumor development is arrested and/or tumor size is reduced. Desirably, the agent causes a 10%, 20%, 30%, 40%, 50%, 60%, 70%, 80%, 90%, 95%, 98%, or 100% decrease in cancer cell proliferation or tumor size when compared to otherwise same conditions wherein a PKAc protein, PKAc fragment, or variant PKAc fragment is not present.

As used here, "effective amount" is used to refer to the amount of a PKAc, fragment or variant fragment required to prevent, inhibit the occurrence, or treat (alleviate a symptom to some extent, preferably all of the symptoms) of a disease state. The effective dose depends on the type of disease, the composition used, the route of administration, the type of animal being treated, the physical characteristics of the specific animal under consideration (e.g., age, weight, gender), concurrent medication, and other factors which those skilled in the medical arts will recognize. Generally, an amount between 0.001 mg/kg and 1000 mg/kg body weight/day of active ingredients is administered dependent upon potency. The invention includes pharmaceutical compositions that include therapeutically- or prophylactically-effective amounts of a therapeutic and a pharmaceutically-acceptable excipient.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci.* USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In so far as the instant compositions decrease or inhibit cancer cell proliferation, individuals having or at risk of having a cancer such as breast cancer, prostate cancer, lung cancer, gastrointestinal tumors, pancreatic cancer, hepatocellular carcinoma, thyroid cancer or CNS malignancies (such as glioblastoma and gliomas) would benefit by receiving treatment with a PKAc protein, PKAc fragment, or variant PKAc fragment. Individuals having cancer generally refer to patients who have been diagnosed with cancer, whereas individuals at risk of having cancer may have a family history of cancer or exhibit one or more signs or symptoms associated with cancer (e.g., a tumor, increased pain perception, weakness). Such individuals, upon receiving treatment with a composition of the present invention, are expected to exhibit a decrease in the signs or symptoms associated with cancer and a general improvement in the quality of life and life expectancy. It is contemplated that not only will the instant compositions be useful in the prevention or treatment of malignancies, said compositions will also find application in the treatment of benign tumors, e.g., benign CNS tumors. While benign CNS tumors do not metastasize, they can cause significant complications and disabilities as the result of their high growth tendency in the skull and putting pressure on the important CNS structures. Thus, treatment with the instant compositions would provide relief from such symptoms.

Given the enhanced cell targeting activity of a PKAc fragment (e.g., ZaTa peptide) of the present invention, particular embodiments embrace the use of a PKAc fragment or variant PKAc fragment as a moiety for targeted delivery of a therapeutic or contrast agent to a cell or tissue. As such, the instant PKAc fragment or variant PKAc fragment can be operatively linked, e.g., via a covalent attachment, to a chemotherapy or therapeutic agent to increase cellular targeting and uptake of the agent as compared to the unconjugated agent. Alternatively, the PKAc fragment or variant PKAc fragment can be attached to the surface of a drug-loaded liposome or nanoparticle for facilitating delivery of drug to a cell. Agents which can be targeted to a cell (e.g., a cancer cell or neuron) using a PKAc fragment or variant PKAc fragment of the invention include cytotoxic agents such as Taxol, Cytochalasin B, Gramicidin D, Ethidium Bromide, Emetine, Mitomycin, Etoposide, Tenoposide, Vincristine, Vinblastine, camptothecin (CPT), Colchicin, Doxorubicin, Daunorubicin, Mitoxantrone, Mithramycin, Actinomycin D, 1-Dehydrotestosterone, Glucocorticoids, Procaine, Tetracaine, Lidocaine, Propranolol, and Puromycin; therapeutic agents including antimetabolites (e.g., Methotrexate, 6-Mercaptopurine, 6-Thioguanine, Cytarabine, 5-Fluorouracil, Decarbazine), alkylating agents (e.g., Mechlorethamine, Thiotepa, Chlorambucil, Melphalan, Carmustine (BCNU), Lomustine (CCNU), Cyclophosphamide, Busulfan, Dibromomannitol, Streptozotocin, Mitomycin C, Cis-Dichlorodiamine Platinum (II) (DDP), Cisplatin), anthracyclines (e.g., Daunorubicin (formerly Daunomycin) and Doxorubicin), antibiotics (e.g., Dactinomycin (formerly Actinomycin), Bleomycin, Mithramycin, and Anthramycin (AMC)), anti-inflammatory agents, anti-mitotic agents (e.g., Vincristine and Vinblastine) and selective apoptotic agents such as APTOSYN® (Exisulind), PANZEM™ (2-methoxyestradiol), VELCADE® (bortezomib) a proteasome inhibitor, cytotoxic agents, alkylating agent, antimetabolite, anthracycline, plant alkaloid, topoisomerase inhibitor, antibody, kinase inhibitor, or other antitumour agents, radioisotopes, therapeutic nucleic acids or polypeptides, fluorescent markers, paramagnetic ions, contrast reagents, metal chelators, toxins, hormones such as steroids; antimetabolites such as cytosine arabinoside, fluorouracil, methotrexate or aminopterin; anthracycline; mitomycin C; vinca alkaloids; demecolcine; etoposide; mithramycin; or alkylating agents such as chlorambucil or melphalan, chemotherapeutic agents, such as anti-tumor drugs, nucleic acids, nucleotides, cytokines, antimetabolites, alkylating agents, antineoplastic agents, peptide or pseudopeptide chelating agents (e.g., linker-chelator, glycyl-tyrosyl-(N,e-diethylenetriaminepentaacetic-acid)-lysine hydrochloride (GYK-DTPA-HCl), radioactive compounds, diphtheria toxin (chain A), ricin toxin (chain A), adriamycin, chlorambucil, daunorubicin, or pokeweed antiviral protein to enhance their tumoricidal effectiveness, nuclear magnetic spin-resonance isotopes, metallic ions, and the like. However, as would be understood by those of skill in the art, the invention is not limited to any particular type or class of therapeutic agent, or any particular disease to be treated.

Methods for performing conjugation of the agents listed above to a peptide or pseudopeptide are well known or readily determinable, and include, for example, conjugation to amino acid side chains, functional groups, carbohydrates, lipids, and other small molecules. See for example, Goldenberg, D. M. et al, New England J. Med., 298:1384-1388 (1978), Goldenberg, D. M. et al, J. A. M. A., 250:630-635 (1983), Goldenberg. D. M. et al, Gastroenterol., 84:524-532 (1983), Siccardi, A. G. et al, Cancer Res., 46:4817-4822 (1986). Epenetos, A. A. et al, Cancer, 55:984-987 (1985), Philben, V. J. et al, Cancer, 57:571-576 (1986), Chiou, R. et al, Cancer Res., 45:6140-6146 (1985) and Hwang, K. M. et al, J. Natl. Cancer Inst., 76:849-855 (1986), all of which are specifically incorporated herein by reference.

Examples of markers which can be conjugated to the antibody are well known to those skilled in the art and include substances which can be detected by nuclear magnetic resonance imaging, i.e., nuclear magnetic spin-resonance isotopes, and radioactive substances. A preferred example of a nuclear magnetic spin-resonance isotope is gadolinium (Gd). Suitable examples of radioactive markers include $I^{125}$, $I^{131}$, $I^{123}$, $In^{111}$, $In^{113}$, $Ga^{67}$, $Ga^{68}$, $Ru^{97}$, $Ru^{103}$, $Hg^{197}$, $Hg^{203}$, and $Tc^{99}$. Detection of radioactive markers is by means of a gamma scintillation camera or the like as described in the references cited above. Nuclear magnetic imaging devices can be used to detect nuclear magnetic spin-resonance isotope markers.

In general, a PKAc fragment of the present invention has an amphipathic nature with a net positive charge. Generally, amphipathic structures play an important role in mediating the interaction of peptides and proteins with membranes (Sharadadevi, et al. (2005) *Proteins* 59:791-801). Because primary amphipathic cell penetrating peptides have been used for the efficient intracellular delivery of large hydrophilic molecules such as oligonucleotides and proteins, they have been used in drug delivery (Plenat, et al. (2005) *Biophys. J.* 89:4300-4309). It has been shown that in amphipathic helices there is a strong preference for Arg or Lys to occur (Sharadadevi, et al. (2005) supra). There is also a relationship between the net charge and average hydrophobic moments, the determining factor for the membrane seeking properties. A net positive charge appears to favor higher hydrophobic moment than a net negative charge (Sharadadevi, et al. (2005) supra). Like known cell penetrating peptides, the amphipathic structure of PKAc fragments such as ZaTa peptide can facilitate penetration into the cell, targeting AKT and PKAc inside the cell and exerting its biological activity. Mutations of Thr-14 or Tyr-17 to Arg generates a higher net positive charge thereby increasing the average hydrophobic moments for ZaTa and augmenting its effect, whereas the mutations of Thr-8 or 10 to the negatively charged Asp causes a less positive net charge, thereby moderating biological activity. Accordingly, the instant PKAc fragment and variant PKAc fragment are useful not only as anticancer agents, but also for targeted delivery of an additional therapeutic agents to a cell.

As in cancer, an increase in the activity of AKT is also known to be associated with different types of Alzheimer's disease (Blain and Massague, (2002) supra; Griffin, et al. (2005) supra; Liang, et al. (2002) supra; Shin, et al. (2002) supra; Viglietto, et al. (2002) supra), wherein reduced AKT activity is related to schizophrenia (Emamian, et al. (2004) supra). Moreover, the PKA signaling pathway has a novel role for in schizophrenia as well (Millar, et al. (2005) supra).

Regarding neuronal synapse activity and neurodegeneration, ion channels have been identified as a novel class of PKB/Akt substrates, pinpointing synaptic plasticity as a biological process regulated by this kinase. In particular, the □2 subunit of the type A—aminobutyric acid ($GABA_A$) receptor is an AKT substrate in vitro and in vivo (Wang, et al. (2002) Neuron 38:915-928). This protein is a member of a ligand-gated chloride ion channel that mediates synaptic transmission at most inhibitory synapses in the mammalian brain. Drugs such as benzodiazapines and barbiturates act on the $GABA_A$ receptor to mediate anti-psychotic effects. AKT-mediated phosphorylation of Ser-410 increases the number of $GABA_A$ receptors on the plasma membrane surface, thereby increasing the efficacy of receptor-mediated inhibition at GABAergic synapses (Brazil, et al. (2004) supra).

Studies in humans provide evidence of increased AKT activation and hyperphosphorylation of critical AKT substrates in Alzheimer's disease (AD) brain (Griffin, et al. (2005) supra). Differential distribution of AKT and phospho-AKT is observed in AD temporal cortex neurons compared with control neurons, which is accompanied with increased levels of active phosphorylated-AKT in particulate fractions, and significant decreases in AKT levels in AD cytosolic fractions, causing increased activation of AKT (phosphorylated-AKT/total AKT ratio) in AD. Further, significant increases in the levels of phosphorylation of total AKT substrates, including GSK3□(Ser-9), tau(Ser-214), mTOR(Ser-2448), and decreased levels of the AKT target, $p27^{Kip1}$, is reported in AD temporal cortex compared with controls. Moreover, a significant loss and altered distribution of the major negative regulator of AKT, PTEN (phosphatase and tensin homologue deleted on chromosome 10), is found in AD neurons. Loss of phosphorylated-AKT and PTEN-containing neurons is observed in hippocampal CA1 at the end stages of AD (Griffin, et al. (2005) supra). Enzymatic activity of AKT in mid-temporal and mid-frontal cortices from AD cases and matched controls has also been analyzed (Rickle, et al. (2004) Neuroreport 15:955-959). The results of this analysis indicated that the activity of AKT (GSK-3□/□ fusion protein phosphorylation by immunoprecipitated AKT) was significantly increased in temporal cortex soluble fractions from AD compared with non-disease controls and positive disease controls with another neurodegenerative disease. Moreover, AKT activity in temporal cortex soluble fractions was positively correlated with Braak staging for neurofibrillary changes. Strong phospho-AKT immunoreactivity was shown in AD pyramidal neurons undergoing degeneration and in reactive astroglia. Given that PKAc fragments can potently decrease AKT substrate phosphorylation in the brain, inhibition of AKT could reverse the observed changes in humans with AD thereby providing therapeutic benefit in the treatment of AD.

Many inherited neurodegenerative diseases are caused by the expansion of a CAG repeat that produces a long polyglutamine (polyQ) tract in proteins, the length of which is directly correlated with the severity of the disease (Emamian, et al. (2003) Neuron 38:375-387; Chen, et al (2003) Cell 113:457-68). AKT substrates that mediate the pathophysiology of spinocerebellar ataxia type 1 (SCA1) and Huntington's disease have been identified (Humbert, et al. (2002) Dev. Cell 2:831-837; Emamian, et al. (2003) supra; Chen, et al. (2003) supra). Toxicity of the mutant proteins in vivo is directly mediated by phosphorylation of Ser-776 (Emamian, et al. (2003) supra). Replacing Ser-776 with Ala completely averts the pathology in vivo, even in the presence of a long polyglutamine tract. Therefore, while polyglutamine expansion is required for the disease to develop, it is not sufficient. Based on this analysis, Ser-776 was identified as a site of AKT phosphorylation, a molecular event that is essential for the interaction of 14-3-3 with the polyQ-expanded form ataxin-1 (Chen, et al. (2003) supra), wherein binding to 14-3-3 triggers the formation of inclusion bodies of ataxin-1, mediating its neurotoxicity. In this regard, PKB/Akt-mediated phosphorylation of the mutant form of ataxin-1 in SCA1 triggers 14-3-3 binding, gradual accumulation of this protein, and consequent neurodegeneration.

Similar to SCA1, Huntington's disease is characterized by an expanded polyQ repeat in the huntingtin protein, which leads to an aggregation of mutated protein in the nucleus and selective apoptosis of striatal neurons in the brain (Saudou, et al. (1998) Cell 95:55-66). In contrast to its role in SCA1, however, AKT positively regulates the survival of striatal neurons lost during the degeneration seen in Huntington's disease. Both insulin-like growth factor 1 (IGF-1) treatment and AKT activation of striatal neurons inhibits cell death and intranuclear inclusion formation mediated by the mutated huntingtin protein (Humbert, et al. (2002) supra). Phosphorylation of the mutated form of huntingtin by PKB/Akt on Ser-421 is required for IGF-1-mediated inhibition of intranuclear inclusion formation and cell death, indicating that compromised AKT activity could accentuate the progression of Huntington's disease. In this regard, analysis of AKT protein in brain samples from individuals affected with Huntington's disease reveals the presence of both full-length AKT (60 kDa) and a shorter form (49 kDa) predicted to be generated by caspase-3-mediated cleavage of the full-length kinase (Humbert, et al. (2002) supra).

AKT signaling in neurons of amyotrophic lateral sclerosis has also been determined (Kaspar, et al. (2003) supra). IGF-1 stimulates the activity of PKB/Akt in the spinal cord and prolongs the lifespan of SOD1 mice by increasing the survival of motor neurons in this setting, indicating that administration of IGF-1 could be of benefit in the treatment of amyotrophic lateral sclerosis (Kaspar, et al. (2003) supra).

Direct evidence has been provided for the role of AKT in axonal growth and the acceleration of axonal regeneration (Markus, et al. (2002) supra; Namikawa, et al. (2000) Nat. Cell Biol. 4:111-116). Furthermore, PKA is also shown to play a role in the axonal pathfinding of zebrafish olfactory sensory neurons (Yoshida, et al. (2002) J. Neurosci. 22:4964-

4972), as well as the ability of axons to regenerate their growth cones (Chierzi, et al. (2005) supra). Having demonstrated that endogenous PKAc co-localizes with AKT in N2a neurons along the neurite length, as well as in the neurite outgrowth zone, and treatment with ZaTa peptide results in a progressive dose-dependent loss of the existing neurites, as well as the inhibition of new neurite formation, methods for modulating neurodegenerative and psychiatric diseases and conditions is also embraced by the present invention. In particular, based on the role of AKT in the pathogenesis of SCA1, Huntington's disease, ALS and AD, PKAc and fragments thereof (e.g., ZaTa peptide) are useful in the prevention and treatment of these neurodegenerative diseases.

Thus, the present invention is also a method for preventing or treating a neurodegenerative disease or disorder using PKAc, or a fragment or variant fragment thereof (e.g., in a pharmaceutical composition). As a prophylactic or therapeutic, an effective amount of the instant composition is administered to a patient having (e.g., showing signs or symptoms of disease) or at risk of having (e.g., genetically predisposed) a neurodegenerative disease or disorder to prevent (i.e., inhibit or delay the development or onset of) or treat (i.e., ameliorate the signs or symptoms of) the disease or disorder. Neurodegenerative diseases or conditions embraced by the present invention include, but are not limited to, SCA1, Huntington's disease, ALS and AD.

Large-scale gene therapy clinical trials for treatment of Parkinson disease are known (Howard (2003) *Nat. Biotechnol.* 21(10):1117-8). In these trials, a gene is cloned into a recombinant expression vector that is known to be deregulated in the disease and is delivered locally to the site of pathology in the brain. Accordingly, it is contemplated that these gene therapy approaches in clinical trials make it possible to use the same settings for the delivery of DNA molecules encoding PKAc proteins or fragments into the site of pathology. This approach can be used to overexpress PKAc proteins or fragments in tumor cells thereby preventing further division and growth, and eventually, resulting in apoptosis and death. As another example, expression of PKAc proteins or fragments in Purkinje cells of the cerebellum using a Purkinje cell-specific promoter (such as PCP-2) and an adenoviral vector system, could be used to inhibit AKT and the phosphorylation of ataxin-1 thereby inhibiting the binding of ataxin-1 with 14-3-3 proteins. As a result, further progression of the pathology is prevented by blocking an upstream critical signal that is required for the development of pathology. As AKT knock out mice do not exhibit a cerebellar dysfunction phenotype, inhibition of AKT in Purkinje cells is not expected to cause side effects, since AKT does not seem to have a crucial role in normal function of cerebellum.

The invention is described in greater detail by the following non-limiting examples.

Example 1

Cell Culture, Protein Extraction, and Immunoblot Analysis

N2a cells were cultured in Dulbecco's Modified Eagle's Medium (DMEM) and OPTI-MEM® media (50% of each; GIBCO-BRL, Gaithersberg, Md.) supplemented with 5% fetal bovine serum (FBS; SIGMA, St. Louis, Mo.), penicillin-streptomycin and L-Glutamine (GIBCO-BRL). Cells (~1× $10^6$) or frontal cortex of mouse brain (0.05-0.1 gram) were homogenized in ice cold lysate buffer (0.25 M Tris, pH 7.5) containing protease inhibitors (Protease Inhibitor Cocktail tablets; Boehringer Mannheim, Mannheim, Germany) and phosphatase inhibitors (Phosphatase Inhibitor Cocktails I & II; SIGMA) and lysed through three cycles of freezing in liquid nitrogen and thawing in a 37° C. water bath. Protein concentration was measured using a commercially available protein assay (BIO-RAD, Waltham, Mass.) protein assay and spectrometry at 595 Å. Equal amounts of total protein were loaded on 4-12% gradient Bis-Tris gels, separated using the NUPAGE® system (INVITROGEN, Carlsbad, Calif.) and transferred onto nitrocellulose membrane. The membrane was probed with primary and secondary antibodies and signals were detected by chemiluminescence followed by autoradiography.

Antibodies included anti-AKT1 (1:1000; Cell Signaling, Beverly, Mass.), anti-GSK3□ (1:5000; Transduction Laboratories, Lexington, Ky.), Ser-9 GSK3□ (1:1000; Cell Signaling) and Tyr-216/Tyr-279 GSK3 phospho-specific antibodies (1:2000; Upstate Biotechnology, Lake Placid, N.Y.), anti-PKAc (1:1000; Cell Signaling or 1:2000; Transduction Laboratories), Thr-308 (1:1000; Cell Signaling) and Ser-473 (1:1000; Cell Signaling), AKT phospho-specific antibodies, anti-AKT (PH domain, 1:2000; Upstate Biotechnology), Thr-34 DARPP-32 and Thr-197 PKAc phospho-specific antibodies (1:1000; Cell Signaling), anti-AKT, -PKA, -PKC, -CDKs substrate-phosphospecific antibodies (1:1000; Cell Signaling), and anti-tubulin (1:5000; SIGMA) as a loading control.)

Phosphorylation sites for kinases analyzed herein included Ser-235/236 S6 (a substrate for p70S6K), Tyr-207 CRKL (a substrate for Abl; Zipfel, et al. (2004) supra), Ser-241 PDK1 (a substrate for PI3K), Tyr-1022/1023 JAK1 (a substrate for JAK3; Wang, et al. (2003) supra), Ser-421 Huntingtin (a substrate for SGK; Rangone, et al. (2004) supra), Tyr-783 PLC (a substrate for TrkB; Middlemas, et al. (1994) supra), and Ser-338 cRaf (a substrate for PAK3; King, et al. (1998) supra).

Example 2

Immunofluorescence Analysis

Cell cultures were analyzed by growing cells ($1\times10^4$) on coverslips, fixation for 10 minutes in phosphate-buffered saline (PBS) plus 3.7% formaldehyde, and permeabilization for 2 minutes with cold acetone. Coverslips were coated with 40 µL of primary antibody diluted in PBS (anti-PKAc monoclonal antibody, 1:200, Transduction Laboratories; anti-AKT-PH domain, 1:200, Upstate Biotechnology; anti-phospho AKT substrate antibody, 1:100, Cell Signaling; and anti-AKT1 antibody, 1:200, Cell Signaling).

For immunofluorescence analysis of mouse brain, anaesthetized mice were perfused with PBS-buffered formalin, fixed overnight, placed in PBS, and stored at 4° C. VIBRATOME® sections, 50-µm thick, were cut in the coronal plane from the fronto-striatum brain region. Epitopes were revealed by microwaving the sections three times for 15 seconds in 0.01 M urea. The sections were blocked overnight using 2% normal goat sera in PBS with 0.3% TRITON™ X-100 and then incubated for 48 hours in blocking solution with 1:500 dilution of anti-phospho-AKT substrate antibody. Sections were washed four times for 15 minutes in PBS, incubated with blocking solution containing goat anti-rabbit ALEXA®-568 secondary antibody (MOLECULAR PROBES, Eugene, Oreg.) for 48 hours, and washed four times for 15 minutes in PBS. Sections were mounted on slides with glycerol-gelatin containing 4 mg/mL n-propylgalate and examined with a ZEISS LSM 5 confocal microscope equipped with a krypton-argon laser. For staining with the nuclear marker, cells or sections were incubated with 1:100 dilution of DRAQ-5 for one hour at room temperature before mounting.

Example 3

In Vitro Kinase Assay

For non-radioactive kinase assays, typically 25 ng of active AKT1 or PKAc (Upstate Biotechnology) was used in a kinase assay reaction buffer (20 mM MOPS, pH 7.2, 25 mM ☐-glycerophosphate, 5 mM EGTA, 1 mM $Na_3VO_4$, 1 mM dithiothreitol, 75 mM $MgCl_2$, and 0.5 mM ATP) in the presence of either 1 μL of Ser-9 GSK-3 GST fusion protein (Cell Signaling), or recombinant DARPP-32 (10 μg). For the radioactive kinase assays, typically 25 ng of kinase was added to the kinase assays reaction buffer (20 mM MOPS, pH 7.2, 25 mM ☐-glycerophosphate, 5 mM EGTA, 1 mM $Na_3VO_4$, 1 mM dithiothreitol) containing 30 μM of dephosphorylated Ser-21 GSK-3 substrate peptide (Upstate Biotechnology) in the presence of different concentrations of inhibitor. Reactions were initiated by adding [$-^{32}$P] ATP (10 μCi/reaction) which was diluted in the reaction buffer, plus 500 μM cold ATP and 75 mM $MgCl_2$. Kinase reactions were incubated 30° C. for 10-20 minutes. A 5 μL aliquot of the reaction was transferred to phosphocellulose paper, washed for 30 minutes with $dH_2O$, and CPM of samples read in scintillation counter.

Example 4

MTT Cell Proliferation Assay

Cells ($5\times10^3$) were incubated in 96-well plates in the presence of different concentrations of the ZaTa peptide, control peptide or DMSO as vehicle. Media was removed at different time intervals and replaced with media containing MTT (5 mg/mL), and incubated for one hour at 37° C. Purple-blue MTT formazan precipitate was dissolved in 100 μL. The activity of the mitochondria, reflecting cellular growth and viability, was evaluated by measuring the optical density at 490 nm on a plate reader.

---

What is claimed is:

1. A composition comprising one or more peptide(s), wherein the peptide(s) is a PKAc fragment or variant thereof selected from the group consisting of;
   (a) the peptide of SEQ ID NO: 60; and
   (b) a peptide variant that has at least 40% identity with SEQ ID NO: 60 and inhibits human AKT1.

2. The composition of claim 1, wherein the peptide variant comprises an arginine substitution at position 14 and/or 17 of SEQ ID NO: 60.

3. The composition of claim 1, wherein the peptide or peptide variant is comprised within a fusion protein having additional peptide(s) or polypeptide(s) located at the N- and/or C-terminus of the peptide or peptide variant.

4. The composition of claim 1, wherein the peptide or peptide variant further comprises an amino acid modification selected from the group consisting of phosphorylation, acetylation, and methylation.

5. An in vitro or cell culture method for inhibiting the activity of AKT1 or p70S6K using the composition of claim 1.

6. A cell culture method for inhibiting cell proliferation using the composition of claim 1.

7. The composition of claim 1, further comprising a carrier, wherein the carrier allows for the controlled, local release of the therapeutic peptide(s).

8. The composition of claim 1, wherein the peptide is as set forth by SEQ ID NO: 60.

\* \* \* \* \*

SEQUENCE LISTING

<160> NUMBER OF SEQ ID NOS: 104

<210> SEQ ID NO 1
<211> LENGTH: 351
<212> TYPE: PRT
<213> ORGANISM: Homo sapiens
<220> FEATURE:
<221> NAME/KEY: MISC_FEATURE
<222> LOCATION: (1)..(351)
<300> PUBLICATION INFORMATION:
<308> DATABASE ACCESSION NUMBER: NP_002721
<309> DATABASE ENTRY DATE: 2009-09-28
<313> RELEVANT RESIDUES IN SEQ ID NO: (1)..(351)

<400> SEQUENCE: 1

```
Met Gly Asn Ala Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Ser Pro Ala Gln Asn Thr Ala His Leu Asp Gln Phe Glu Arg Ile Lys
        35                  40                  45

Thr Leu Gly Thr Gly Ser Phe Gly Arg Val Met Leu Val Lys His Lys
    50                  55                  60

Glu Thr Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Pro Gly Gly Glu
        115                 120                 125

Met Phe Ser His Leu Arg Arg Ile Gly Arg Phe Ser Glu Pro His Ala
    130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
```

```
                180                 185                 190
Lys Gly Arg Thr Trp Thr Leu Cys Gly Thr Pro Glu Tyr Leu Ala Pro
                    195                 200                 205

Glu Ile Ile Leu Ser Lys Gly Tyr Asn Lys Ala Val Asp Trp Trp Ala
        210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
        260                 265                 270

Leu Leu Gln Val Asp Leu Thr Lys Arg Phe Gly Asn Leu Lys Asn Gly
                275                 280                 285

Val Asn Asp Ile Lys Asn His Lys Trp Phe Ala Thr Thr Asp Trp Ile
290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Ile
                325                 330                 335

Arg Val Ser Ile Asn Glu Lys Cys Gly Lys Glu Phe Ser Glu Phe
                340                 345                 350

<210> SEQ ID NO 2
<211> LENGTH: 343
<212> TYPE: PRT
<213> ORGANISM: Homo sapiens
<220> FEATURE:
<221> NAME/KEY: MISC_FEATURE
<222> LOCATION: (1)..(343)
<300> PUBLICATION INFORMATION:
<308> DATABASE ACCESSION NUMBER: NP_997401
<309> DATABASE ENTRY DATE: 2009-09-28
<313> RELEVANT RESIDUES IN SEQ ID NO: (1)..(343)

<400> SEQUENCE: 2

Met Ala Ser Asn Ser Ser Asp Val Lys Glu Phe Leu Ala Lys Ala Lys
1               5                   10                  15

Glu Asp Phe Leu Lys Lys Trp Glu Ser Pro Ala Gln Asn Thr Ala His
            20                  25                  30

Leu Asp Gln Phe Glu Arg Ile Lys Thr Leu Gly Thr Gly Ser Phe Gly
        35                  40                  45

Arg Val Met Leu Val Lys His Lys Glu Thr Gly Asn His Tyr Ala Met
    50                  55                  60

Lys Ile Leu Asp Lys Gln Lys Val Val Lys Leu Lys Gln Ile Glu His
65                  70                  75                  80

Thr Leu Asn Glu Lys Arg Ile Leu Gln Ala Val Asn Phe Pro Phe Leu
                85                  90                  95

Val Lys Leu Glu Phe Ser Phe Lys Asp Asn Ser Asn Leu Tyr Met Val
            100                 105                 110

Met Glu Tyr Val Pro Gly Gly Glu Met Phe Ser His Leu Arg Arg Ile
        115                 120                 125

Gly Arg Phe Ser Glu Pro His Ala Arg Phe Tyr Ala Ala Gln Ile Val
    130                 135                 140

Leu Thr Phe Glu Tyr Leu His Ser Leu Asp Leu Ile Tyr Arg Asp Leu
145                 150                 155                 160

Lys Pro Glu Asn Leu Leu Ile Asp Gln Gln Gly Tyr Ile Gln Val Thr
                165                 170                 175
```

```
Asp Phe Gly Phe Ala Lys Arg Val Lys Gly Arg Thr Trp Thr Leu Cys
            180                 185                 190
Gly Thr Pro Glu Tyr Leu Ala Pro Glu Ile Ile Leu Ser Lys Gly Tyr
        195                 200                 205
Asn Lys Ala Val Asp Trp Trp Ala Leu Gly Val Leu Ile Tyr Glu Met
    210                 215                 220
Ala Ala Gly Tyr Pro Pro Phe Ala Asp Gln Pro Ile Gln Ile Tyr
225                 230                 235                 240
Glu Lys Ile Val Ser Gly Lys Val Arg Phe Pro Ser His Phe Ser Ser
                245                 250                 255
Asp Leu Lys Asp Leu Leu Arg Asn Leu Leu Gln Val Asp Leu Thr Lys
            260                 265                 270
Arg Phe Gly Asn Leu Lys Asn Gly Val Asn Asp Ile Lys Asn His Lys
        275                 280                 285
Trp Phe Ala Thr Thr Asp Trp Ile Ala Ile Tyr Gln Arg Lys Val Glu
    290                 295                 300
Ala Pro Phe Ile Pro Lys Phe Lys Gly Pro Gly Asp Thr Ser Asn Phe
305                 310                 315                 320
Asp Asp Tyr Glu Glu Glu Ile Arg Val Ser Ile Asn Glu Lys Cys
                325                 330                 335
Gly Lys Glu Phe Ser Glu Phe
            340

<210> SEQ ID NO 3
<211> LENGTH: 351
<212> TYPE: PRT
<213> ORGANISM: Bos taurus
<220> FEATURE:
<221> NAME/KEY: MISC_FEATURE
<222> LOCATION: (1)..(351)
<300> PUBLICATION INFORMATION:
<308> DATABASE ACCESSION NUMBER: CAA47627
<309> DATABASE ENTRY DATE: 1993-06-30
<313> RELEVANT RESIDUES IN SEQ ID NO: (1)..(351)

<400> SEQUENCE: 3

Met Gly Asn Ala Ala Ala Ala Lys Lys Gly Ser Glu Gln Glu Ser Val
1               5                   10                  15
Lys Glu Phe Leu Ala Lys Ala Lys Glu Asp Phe Leu Lys Lys Trp Glu
            20                  25                  30
Asn Pro Ala Gln Asn Thr Ala His Leu Asp Gln Phe Glu Arg Ile Lys
        35                  40                  45
Thr Leu Gly Thr Gly Ser Phe Gly Arg Val Met Leu Val Lys His Met
    50                  55                  60
Glu Thr Gly Asn His Tyr Ala Met Lys Ile Leu Asp Lys Gln Lys Val
65                  70                  75                  80
Val Lys Leu Lys Gln Ile Glu His Thr Leu Asn Glu Lys Arg Ile Leu
                85                  90                  95
Gln Ala Val Asn Phe Pro Phe Leu Val Lys Leu Glu Phe Ser Phe Lys
            100                 105                 110
Asp Asn Ser Asn Leu Tyr Met Val Met Glu Tyr Val Pro Gly Gly Glu
        115                 120                 125
Met Phe Ser His Leu Arg Arg Ile Gly Arg Phe Ser Glu Pro His Ala
    130                 135                 140
Arg Phe Tyr Ala Ala Gln Ile Val Leu Thr Phe Glu Tyr Leu His Ser
145                 150                 155                 160
Leu Asp Leu Ile Tyr Arg Asp Leu Lys Pro Glu Asn Leu Leu Ile Asp
                165                 170                 175
```

```
Gln Gln Gly Tyr Ile Gln Val Thr Asp Phe Gly Phe Ala Lys Arg Val
            180                 185                 190
Lys Gly Arg Thr Trp Thr Leu Cys Gly Thr Pro Glu Tyr Leu Ala Pro
        195                 200                 205
Glu Ile Ile Leu Ser Lys Gly Tyr Asn Lys Ala Val Asp Trp Trp Ala
    210                 215                 220
Leu Gly Val Leu Ile Tyr Glu Met Ala Ala Gly Tyr Pro Pro Phe Phe
225                 230                 235                 240
Ala Asp Gln Pro Ile Gln Ile Tyr Glu Lys Ile Val Ser Gly Lys Val
            245                 250                 255
Arg Phe Pro Ser His Phe Ser Ser Asp Leu Lys Asp Leu Leu Arg Asn
        260                 265                 270
Leu Leu Gln Val Asp Leu Thr Lys Arg Phe Gly Asn Leu Lys Asn Gly
    275                 280                 285
Val Asn Asp Ile Lys Asn His Lys Trp Phe Ala Thr Thr Asp Trp Ile
290                 295                 300
Ala Ile Tyr Gln Arg Lys Val Glu Ala Pro Phe Ile Pro Lys Phe Lys
305                 310                 315                 320
Gly Pro Gly Asp Thr Ser Asn Phe Asp Asp Tyr Glu Glu Glu Glu Ile
            325                 330                 335
Arg Val Ser Ile Asn Glu Lys Cys Gly Lys Glu Phe Ser Glu Phe
        340                 345                 350

<210> SEQ ID NO 4
<211> LENGTH: 350
<212> TYPE: PRT
<213> ORGANISM: Canis familiaris
<220> FEATURE:
<221> NAME/KEY: MISC_FEATURE
<222> LOCATION: (1)..(350)
<300> PUBLICATION INFORMATION:
<308> DATABASE ACCESSION NUMBER: NP_001003032
<309> DATABASE ENTRY DATE: 2009-05-10
<313> RELEVANT RESIDUES IN SEQ ID NO: (1)..(350)

<400> SEQUENCE: 4

Met Gly Asn Ala Ala Ala Lys Lys Gly Ser Glu Gln Glu Ser Val Lys
1               5                   10                  15
Glu Phe Leu Ala Lys Ala Lys Glu Asp Phe Leu Lys Lys Trp Glu Asn
            20                  25                  30
Pro Ala Gln Asn Thr Ala His Leu Asp Gln Phe Glu Arg Ile Lys Thr
        35                  40                  45
Leu Gly Thr Gly Ser Phe Gly Arg Val Met Leu Val Lys His Lys Glu
    50                  55                  60
Thr Gly Asn His Phe Ala Met Lys Ile Leu Asp Lys Gln Lys Val Val
65                  70                  75                  80
Lys Leu Lys Gln Ile Glu His Thr Leu Asn Glu Lys Arg Ile Leu Gln
            85                  90                  95
Ala Val Asn Phe Pro Phe Leu Val Lys Leu Glu Phe Ser Phe Lys Asp
        100                 105                 110
Asn Ser Asn Leu Tyr Met Val Met Glu Tyr Val Pro Gly Gly Glu Met
    115                 120                 125
Phe Ser His Leu Arg Arg Ile Gly Arg Phe Ser Glu Pro His Ala Arg
130                 135                 140
Phe Tyr Ala Ala Gln Ile Val Leu Thr Phe Glu Tyr Leu His Ser Leu
145                 150                 155                 160
Asp Leu Ile Tyr Arg Asp Leu Lys Pro Glu Asn Leu Leu Ile Asp Gln
```

```
                165                 170                 175
Gln Gly Tyr Ile Gln Val Thr Asp Phe Gly Phe Ala Lys Arg Val Lys
            180                 185                 190

Gly Arg Thr Trp Thr Leu Cys Gly Thr Pro Glu Tyr Leu Ala Pro Glu
        195                 200                 205

Ile Ile Leu Ser Lys Gly Tyr Asn Lys Ala Val Asp Trp Trp Ala Leu
    210                 215                 220

Gly Val Leu Ile Tyr Glu Met Ala Ala Gly Tyr Pro Pro Phe Phe Ala
225                 230                 235                 240

Asp Gln Pro Ile Gln Ile Tyr Glu Lys Ile Val Ser Gly Lys Val Arg
            245                 250                 255

Phe Pro Ser His Phe Ser Ser Asp Leu Lys Asp Leu Leu Arg Asn Leu
        260                 265                 270

Leu Gln Val Asp Leu Thr Lys Arg Phe Gly Asn Leu Lys Asn Gly Val
    275                 280                 285

Asn Asp Ile Lys Asn His Lys Trp Phe Ala Thr Thr Asp Trp Ile Ala
290                 295                 300

Ile Tyr Gln Arg Lys Val Glu Ala Pro Phe Ile Pro Lys Phe Lys Gly
305                 310                 315                 320

Pro Gly Asp Thr Ser Asn Phe Asp Asp Tyr Glu Glu Glu Ile Arg
            325                 330                 335

Val Ser Ile Asn Glu Lys Cys Gly Lys Glu Phe Cys Glu Phe
            340                 345                 350

<210> SEQ ID NO 5
<211> LENGTH: 351
<212> TYPE: PRT
<213> ORGANISM: Mus musculus
<220> FEATURE:
<221> NAME/KEY: MISC_FEATURE
<222> LOCATION: (1)..(351)
<300> PUBLICATION INFORMATION:
<308> DATABASE ACCESSION NUMBER: NP_032880
<309> DATABASE ENTRY DATE: 2009-10-04
<313> RELEVANT RESIDUES IN SEQ ID NO: (1)..(351)

<400> SEQUENCE: 5

Met Gly Asn Ala Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Thr Pro Ser Gln Asn Thr Ala Gln Leu Asp Gln Phe Asp Arg Ile Lys
        35                  40                  45

Thr Leu Gly Thr Gly Ser Phe Gly Arg Val Met Leu Val Lys His Lys
    50                  55                  60

Glu Ser Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
            85                  90                  95

Gln Ala Val Asn Phe Pro Phe Leu Val Lys Leu Glu Phe Ser Phe Lys
        100                 105                 110

Asp Asn Ser Asn Leu Tyr Met Val Met Glu Tyr Val Ala Gly Gly Glu
    115                 120                 125

Met Phe Ser His Leu Arg Arg Ile Gly Arg Phe Ser Glu Pro His Ala
130                 135                 140

Arg Phe Tyr Ala Ala Gln Ile Val Leu Thr Phe Glu Tyr Leu His Ser
145                 150                 155                 160
```

```
Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
        195                 200                 205

Glu Ile Ile Leu Ser Lys Gly Tyr Asn Lys Ala Val Asp Trp Trp Ala
    210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
        275                 280                 285

Val Asn Asp Ile Lys Asn His Lys Trp Phe Ala Thr Thr Asp Trp Ile
    290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
                325                 330                 335

Arg Val Ser Ile Asn Glu Lys Cys Gly Lys Glu Phe Thr Glu Phe
            340                 345                 350

<210> SEQ ID NO 6
<211> LENGTH: 351
<212> TYPE: PRT
<213> ORGANISM: Rattus norvegicus
<220> FEATURE:
<221> NAME/KEY: MISC_FEATURE
<222> LOCATION: (1)..(351)
<300> PUBLICATION INFORMATION:
<308> DATABASE ACCESSION NUMBER: P27791
<309> DATABASE ENTRY DATE: 2009-10-13
<313> RELEVANT RESIDUES IN SEQ ID NO: (1)..(351)

<400> SEQUENCE: 6

Met Gly Asn Ala Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Asp Pro Ser Gln Asn Thr Ala Gln Leu Asp His Phe Asp Arg Ile Lys
        35                  40                  45

Thr Leu Gly Thr Gly Ser Phe Gly Arg Val Met Leu Val Lys His Lys
    50                  55                  60

Glu Ser Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Pro Gly Gly Glu
        115                 120                 125

Met Phe Ser His Leu Arg Arg Ile Gly Arg Phe Ser Glu Pro His Ala
    130                 135                 140

Arg Phe Tyr Ala Ala Gln Ile Val Leu Thr Phe Glu Tyr Leu His Ser
145                 150                 155                 160
```

```
Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
        195                 200                 205

Glu Ile Ile Leu Ser Lys Gly Tyr Asn Lys Ala Val Asp Trp Trp Ala
    210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
        275                 280                 285

Val Asn Asp Ile Lys Asn His Lys Trp Phe Ala Thr Thr Asp Trp Ile
    290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Ile
                325                 330                 335

Arg Val Ser Ile Asn Glu Lys Cys Gly Lys Glu Phe Thr Glu Phe
            340                 345                 350

<210> SEQ ID NO 7
<211> LENGTH: 343
<212> TYPE: PRT
<213> ORGANISM: Artificial
<220> FEATURE:
<223> OTHER INFORMATION: Synthetic/consensus sequence
<220> FEATURE:
<221> NAME/KEY: MISC_FEATURE
<222> LOCATION: (1)..(2)
<223> OTHER INFORMATION: Xaa = any amino acid
<220> FEATURE:
<221> NAME/KEY: MISC_FEATURE
<222> LOCATION: (4)..(7)
<223> OTHER INFORMATION: Xaa = any amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: MISC_FEATURE
<222> LOCATION: (32)..(32)
<223> OTHER INFORMATION: Xaa = any amino acid
<220> FEATURE:
<221> NAME/KEY: MISC_FEATURE
<222> LOCATION: (35)..(35)
<223> OTHER INFORMATION: Xaa = any amino acid
<220> FEATURE:
<221> NAME/KEY: MISC_FEATURE
<222> LOCATION: (37)..(37)
<223> OTHER INFORMATION: Xaa = any amino acid
<220> FEATURE:
<221> NAME/KEY: MISC_FEATURE
<222> LOCATION: (56)..(56)
<223> OTHER INFORMATION: Xaa = any amino acid
<220> FEATURE:
<221> NAME/KEY: MISC_FEATURE
<222> LOCATION: (62)..(62)
<223> OTHER INFORMATION: Xaa = any amino acid
```

```
<220> FEATURE:
<221> NAME/KEY: MISC_FEATURE
<222> LOCATION: (341)..(341)
<223> OTHER INFORMATION: Xaa = any amino acid

<400> SEQUENCE: 7

Xaa Xaa Ser Xaa Xaa Xaa Val Lys Glu Phe Leu Ala Lys Ala Lys
1               5                   10                  15

Glu Asp Phe Leu Lys Lys Trp Glu Xaa Pro Xaa Gln Asn Thr Ala Xaa
            20                  25                  30

Leu Asp Xaa Phe Xaa Arg Ile Lys Thr Leu Gly Thr Gly Ser Phe Gly
        35                  40                  45

Arg Val Met Leu Val Lys His Xaa Glu Thr Gly Asn His Xaa Ala Met
50                  55                  60

Lys Ile Leu Asp Lys Gln Lys Val Val Lys Leu Lys Gln Ile Glu His
65                  70                  75                  80

Thr Leu Asn Glu Lys Arg Ile Leu Gln Ala Val Asn Phe Pro Phe Leu
                85                  90                  95

Val Lys Leu Glu Phe Ser Phe Lys Asp Asn Ser Asn Leu Tyr Met Val
            100                 105                 110

Met Glu Tyr Val Pro Gly Gly Glu Met Phe Ser His Leu Arg Arg Ile
        115                 120                 125

Gly Arg Phe Ser Glu Pro His Ala Arg Phe Tyr Ala Ala Gln Ile Val
130                 135                 140

Leu Thr Phe Glu Tyr Leu His Ser Leu Asp Leu Ile Tyr Arg Asp Leu
145                 150                 155                 160

Lys Pro Glu Asn Leu Leu Ile Asp Gln Gln Gly Tyr Ile Gln Val Thr
                165                 170                 175

Asp Phe Gly Phe Ala Lys Arg Val Lys Gly Arg Thr Trp Thr Leu Cys
            180                 185                 190

Gly Thr Pro Glu Tyr Leu Ala Pro Glu Ile Ile Leu Ser Lys Gly Tyr
        195                 200                 205

Asn Lys Ala Val Asp Trp Trp Ala Leu Gly Val Leu Ile Tyr Glu Met
210                 215                 220

Ala Ala Gly Tyr Pro Pro Phe Phe Ala Asp Gln Pro Ile Gln Ile Tyr
225                 230                 235                 240

Glu Lys Ile Val Ser Gly Lys Val Arg Phe Pro Ser His Phe Ser Ser
                245                 250                 255

Asp Leu Lys Asp Leu Leu Arg Asn Leu Leu Gln Val Asp Leu Thr Lys
            260                 265                 270

Arg Phe Gly Asn Leu Lys Asn Gly Val Asn Asp Ile Lys Asn His Lys
        275                 280                 285

Trp Phe Ala Thr Thr Asp Trp Ile Ala Ile Tyr Gln Arg Lys Val Glu
290                 295                 300

Ala Pro Phe Ile Pro Lys Phe Lys Gly Pro Gly Asp Thr Ser Asn Phe
305                 310                 315                 320

Asp Asp Tyr Glu Glu Glu Glu Ile Arg Val Ser Ile Asn Glu Lys Cys
                325                 330                 335

Gly Lys Glu Phe Xaa Glu Phe
            340

<210> SEQ ID NO 8
<211> LENGTH: 16
<212> TYPE: PRT
<213> ORGANISM: Artificial Sequence
<220> FEATURE:
<223> OTHER INFORMATION: Synthetic Peptide
```

```
-continued

<220> FEATURE:
<221> NAME/KEY: MISC_FEATURE
<222> LOCATION: (1)..(16)
<223> OTHER INFORMATION: Peptide_SEQ ID NO.8

<400> SEQUENCE: 8

Met Gly Asn Ala Ala Ala Ala Lys Lys Gly Ser Glu Gln Glu Ser Val
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:9

<400> SEQUENCE: 9

Ala Ala Lys Lys Gly Ser Glu Gln Glu Ser Val Lys Glu Phe Leu
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:10

<400> SEQUENCE: 10

Gly Ser Glu Gln Glu Ser Val Lys Glu Phe Leu Ala Lys Ala Lys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:11

<400> SEQUENCE: 11

Glu Ser Val Lys Glu Phe Leu Ala Lys Ala Lys Glu Asp Phe Leu
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:12

<400> SEQUENCE: 12

Glu Phe Leu Ala Lys Ala Lys Glu Asp Phe Leu Lys Lys Trp
1               5                   10

<210> SEQ ID NO 13
```

-continued

```
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:13

<400> SEQUENCE: 13

Ala Lys Ala Lys Glu Asp Phe Leu Lys Lys Trp Glu Asn Pro Ala
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:14

<400> SEQUENCE: 14

Glu Asp Phe Leu Lys Lys Trp Glu Asn Pro Ala Gln Asn Thr Ala
 1               5                  10                  15

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(13)
<223> OTHER INFORMATION: Peptide_SEQ ID NO:15

<400> SEQUENCE: 15

Lys Lys Trp Glu Asn Pro Ala Gln Asn Thr Ala His Leu
 1               5                  10

<210> SEQ ID NO 16
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:16

<400> SEQUENCE: 16

Trp Glu Asn Pro Ala Gln Asn Thr Ala His Leu Asp Gln Phe
 1               5                  10

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:17

<400> SEQUENCE: 17
```

Pro Ala Gln Asn Thr Ala His Leu Asp Gln Phe Glu Arg Ile Lys
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(13)
<223> OTHER INFORMATION: Peptide_SEQ ID NO:18

<400> SEQUENCE: 18

Thr Ala His Leu Asp Gln Phe Glu Arg Ile Lys Thr Leu
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(16)
<223> OTHER INFORMATION: Peptide_SEQ ID NO:19

<400> SEQUENCE: 19

His Leu Asp Gln Phe Glu Arg Ile Asp Thr Leu Gly Thr Gly Ser Phe
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:20

<400> SEQUENCE: 20

Glu Arg Ile Lys Thr Leu Gly Thr Gly Ser Phe Gly Arg Val Met
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:21

<400> SEQUENCE: 21

Thr Leu Gly Thr Gly Ser Phe Gly Arg Val Met Leu Val Lys His
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<222> LOCATION: (1)..(12)
<223> OTHER INFORMATION: Peptide_SEQ ID NO:22

<400> SEQUENCE: 22

Gly Ser Phe Gly Arg Val Met Leu Val Lys His Met
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(16)
<223> OTHER INFORMATION: Peptide_SEQ ID NO:23

<400> SEQUENCE: 23

Ser Phe Gly Arg Val Met Leu Val Lys His Met Glu Thr Gly Asn His
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:24

<400> SEQUENCE: 24

Met Leu Val Lys His Met Glu Thr Gly Asn His Tyr Ala Met Lys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:25

<400> SEQUENCE: 25

His Met Glu Thr Gly Asn His Tyr Ala Met Lys Ile Leu Asp Lys
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:26

<400> SEQUENCE: 26

Gly Asn His Tyr Ala Met Lys Ile Leu Asp Lys Gln Lys Val Val
1               5                   10                  15

<210> SEQ ID NO 27
<211> LENGTH: 14
<212> TYPE: PRT
```

-continued

<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:27

<400> SEQUENCE: 27

Ala Met Lys Ile Leu Asp Lys Gln Lys Val Val Lys Leu Lys
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:28

<400> SEQUENCE: 28

Ile Leu Asp Lys Gln Lys Val Val Lys Leu Lys Gln Ile Glu His
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:29

<400> SEQUENCE: 29

Lys Gln Lys Val Val Lys Leu Lys Gln Ile Glu His Thr Leu
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:30

<400> SEQUENCE: 30

Val Val Lys Leu Lys Gln Ile Glu His Thr Leu Asn Glu Lys Arg
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:31

<400> SEQUENCE: 31

Lys Gln Ile Glu His Thr Leu Asn Glu Lys Arg Ile Leu Gln Ala
1               5                   10                  15

```
<210> SEQ ID NO 32
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:32

<400> SEQUENCE: 32

His Thr Leu Asn Glu Lys Arg Ile Leu Gln Ala Val Asn Phe
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:33

<400> SEQUENCE: 33

Asn Glu Lys Arg Ile Leu Gln Ala Val Asn Phe Pro Phe Leu Val
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:34

<400> SEQUENCE: 34

Ile Leu Gln Ala Val Asn Phe Pro Phe Leu Val Lys Leu Glu Phe
1               5                   10                  15

<210> SEQ ID NO 35
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:35

<400> SEQUENCE: 35

Val Asn Phe Pro Phe Leu Val Lys Leu Glu Phe Ser Phe Lys
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(16)
<223> OTHER INFORMATION: Peptide_SEQ ID NO:36
```

```
<400> SEQUENCE: 36

Pro Phe Leu Val Lys Leu Glu Phe Ser Phe Lys Asp Asn Ser Asn Leu
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:37

<400> SEQUENCE: 37

Leu Glu Phe Ser Phe Lys Asp Asn Ser Asn Leu Tyr Met Val Met
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:38

<400> SEQUENCE: 38

Phe Lys Asp Asn Ser Asn Leu Tyr Met Val Met Glu Tyr Val
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(16)
<223> OTHER INFORMATION: Peptide_SEQ ID NO:39

<400> SEQUENCE: 39

Asn Ser Asn Leu Tyr Met Val Met Glu Tyr Val Pro Gly Gly Glu Met
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:40

<400> SEQUENCE: 40

Met Val Met Glu Tyr Val Pro Gly Gly Glu Met Phe Ser His Leu
1               5                   10                  15

<210> SEQ ID NO 41
<211> LENGTH: 14
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:41

<400> SEQUENCE: 41

Tyr Val Pro Gly Gly Glu Met Phe Ser His Leu Arg Arg Ile
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:42

<400> SEQUENCE: 42

Gly Gly Glu Met Phe Ser His Leu Arg Arg Ile Gly Arg Phe
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:43

<400> SEQUENCE: 43

Met Phe Ser His Leu Arg Arg Ile Gly Arg Phe Ser Glu Pro His
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:44

<400> SEQUENCE: 44

Leu Arg Arg Ile Gly Arg Phe Ser Glu Pro His Ala Arg Phe Tyr
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:45

<400> SEQUENCE: 45

Gly Arg Phe Ser Glu Pro His Ala Arg Phe Tyr Ala Ala Gln Ile
1               5                   10                  15
```

```
<210> SEQ ID NO 46
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:46

<400> SEQUENCE: 46

Glu Pro His Ala Arg Phe Tyr Ala Ala Gln Ile Val Leu Thr Phe
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:47

<400> SEQUENCE: 47

Arg Phe Tyr Ala Ala Gln Ile Val Leu Thr Phe Glu Tyr Leu His
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:48

<400> SEQUENCE: 48

Ala Gln Ile Val Leu Thr Phe Glu Tyr Leu His Ser Leu Asp Leu
1               5                   10                  15

<210> SEQ ID NO 49
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:49

<400> SEQUENCE: 49

Leu Thr Phe Glu Tyr Leu His Ser Leu Asp Leu Ile Tyr Arg
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:50

<400> SEQUENCE: 50
```

Glu Tyr Leu His Ser Leu Asp Leu Ile Tyr Arg Asp Leu Lys
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:51

<400> SEQUENCE: 51

His Ser Leu Asp Leu Ile Tyr Arg Asp Leu Lys Pro Glu Asn Leu
1               5                   10                  15

<210> SEQ ID NO 52
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(13)
<223> OTHER INFORMATION: Peptide_SEQ ID NO:52

<400> SEQUENCE: 52

Leu Ile Tyr Arg Asp Leu Lys Pro Glu Asn Leu Leu Ile
1               5                   10

<210> SEQ ID NO 53
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(16)
<223> OTHER INFORMATION: Peptide_SEQ ID NO:53

<400> SEQUENCE: 53

Tyr Arg Asp Leu Lys Pro Glu Asn Leu Leu Ile Asp Gln Gln Gly Tyr
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:54

<400> SEQUENCE: 54

Pro Glu Asn Leu Leu Ile Asp Gln Gln Gly Tyr Ile Gln Val
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic peptide
<220> FEATURE:

<221> NAME/KEY: MISC_FEATURE
<222> LOCATION: (1)..(14)
<223> OTHER INFORMATION: Peptide_SEQ ID NO:55

<400> SEQUENCE: 55

Leu Leu Ile Asp Gln Gln Gly Tyr Ile Gln Val Thr Asp Phe
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:56

<400> SEQUENCE: 56

Asp Gln Gln Gly Tyr Ile Gln Val Thr Asp Phe Gly Phe Ala Lys
1               5                   10                  15

<210> SEQ ID NO 57
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:57

<400> SEQUENCE: 57

Tyr Ile Gln Val Thr Asp Phe Gly Phe Ala Lys Arg Val Lys
1               5                   10

<210> SEQ ID NO 58
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:58

<400> SEQUENCE: 58

Val Thr Asp Phe Gly Phe Ala Lys Arg Val Lys Gly Arg Thr Trp
1               5                   10                  15

<210> SEQ ID NO 59
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(13)
<223> OTHER INFORMATION: Peptide_SEQ ID NO:59

<400> SEQUENCE: 59

Gly Phe Ala Lys Arg Val Lys Gly Arg Thr Trp Thr Leu
1               5                   10

<210> SEQ ID NO 60
<211> LENGTH: 17

<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(17)
<223> OTHER INFORMATION: Peptide_SEQ ID NO:60

<400> SEQUENCE: 60

Ala Lys Arg Val Lys Gly Arg Thr Trp Thr Leu Cys Gly Thr Pro Glu
1               5                   10                  15

Tyr

<210> SEQ ID NO 61
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(13)
<223> OTHER INFORMATION: Peptide_SEQ ID NO:61

<400> SEQUENCE: 61

Arg Thr Trp Thr Leu Cys Gly Thr Pro Glu Tyr Leu Ala
1               5                   10

<210> SEQ ID NO 62
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:62

<400> SEQUENCE: 62

Trp Thr Leu Cys Gly Thr Pro Glu Tyr Leu Ala Pro Glu Ile Ile
1               5                   10                  15

<210> SEQ ID NO 63
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:63

<400> SEQUENCE: 63

Gly Thr Pro Glu Tyr Leu Ala Pro Glu Ile Ile Leu Ser Lys
1               5                   10

<210> SEQ ID NO 64
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:64

<400> SEQUENCE: 64

Glu Tyr Leu Ala Pro Glu Ile Ile Leu Ser Lys Gly Tyr Asn Lys
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:65

<400> SEQUENCE: 65

Pro Glu Ile Ile Leu Ser Lys Gly Tyr Asn Lys Ala Val Asp Trp
1               5                   10                  15

<210> SEQ ID NO 66
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:66

<400> SEQUENCE: 66

Leu Ser Lys Gly Tyr Asn Lys Ala Val Asp Trp Trp Ala Leu
1               5                   10

<210> SEQ ID NO 67
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:67

<400> SEQUENCE: 67

Gly Tyr Asn Lys Ala Val Asp Trp Trp Ala Leu Gly Val Leu Ile
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:68

<400> SEQUENCE: 68

Ala Val Asp Trp Trp Ala Leu Gly Val Leu Ile Tyr Glu Met Ala
1               5                   10                  15

<210> SEQ ID NO 69
<211> LENGTH: 14
<212> TYPE: PRT
<213> ORGANISM: Artificial Sequence
<220> FEATURE:
<223> OTHER INFORMATION: Synthetic peptide
<220> FEATURE:

```
<221> NAME/KEY: MISC_FEATURE
<222> LOCATION: (1)..(14)
<223> OTHER INFORMATION: Peptide_SEQ ID NO:69

<400> SEQUENCE: 69

Trp Ala Leu Gly Val Leu Ile Tyr Glu Met Ala Ala Gly Tyr
1               5                   10

<210> SEQ ID NO 70
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:70

<400> SEQUENCE: 70

Gly Val Leu Ile Tyr Glu Met Ala Ala Gly Tyr Pro Pro Phe Phe
1               5                   10                  15

<210> SEQ ID NO 71
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: Peptide_SEQ ID NO:71

<400> SEQUENCE: 71

Tyr Glu Met Ala Ala Gly Tyr Pro Pro Phe Phe Ala
1               5                   10

<210> SEQ ID NO 72
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:72

<400> SEQUENCE: 72

Glu Met Ala Ala Gly Tyr Pro Pro Phe Phe Ala Asp Gln Pro Ile
1               5                   10                  15

<210> SEQ ID NO 73
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:73

<400> SEQUENCE: 73

Gly Tyr Pro Pro Phe Phe Ala Asp Gln Pro Ile Gln Ile Tyr
1               5                   10

<210> SEQ ID NO 74
<211> LENGTH: 15
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:74

<400> SEQUENCE: 74

Pro Phe Phe Ala Asp Gln Pro Ile Gln Ile Tyr Glu Lys Ile Val
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:75

<400> SEQUENCE: 75

Asp Gln Pro Ile Gln Ile Tyr Glu Lys Ile Val Ser Gly Lys Val
1               5                   10                  15

<210> SEQ ID NO 76
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:76

<400> SEQUENCE: 76

Ile Gln Ile Tyr Glu Lys Ile Val Ser Gly Lys Val Arg Phe
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:77

<400> SEQUENCE: 77

Tyr Glu Lys Ile Val Ser Gly Lys Val Arg Phe Pro Ser His Phe
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:78

<400> SEQUENCE: 78

Val Ser Gly Lys Val Arg Phe Pro Ser His Phe Ser Ser Asp Leu
```

```
1               5                   10                  15
```

```
<210> SEQ ID NO 79
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:79

<400> SEQUENCE: 79

Val Arg Phe Pro Ser His Phe Ser Ser Asp Leu Lys Asp Leu Leu
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:80

<400> SEQUENCE: 80

Ser His Phe Ser Ser Asp Leu Lys Asp Leu Leu Arg Asn Leu Leu
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:81

<400> SEQUENCE: 81

Ser Asp Leu Lys Asp Leu Leu Arg Asn Leu Leu Gln Val Asp Leu
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:82

<400> SEQUENCE: 82

Asp Leu Leu Arg Asn Leu Leu Gln Val Asp Leu Thr Lys Arg Phe
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
```

-continued

<223> OTHER INFORMATION: Peptide_SEQ ID NO:83

<400> SEQUENCE: 83

Asn Leu Leu Gln Val Asp Leu Thr Lys Arg Phe Gly Asn Leu Lys
1               5                   10                  15

<210> SEQ ID NO 84
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:84

<400> SEQUENCE: 84

Val Asp Leu Thr Lys Arg Phe Gly Asn Leu Lys Asn Gly Val
1               5                   10

<210> SEQ ID NO 85
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:85

<400> SEQUENCE: 85

Thr Lys Arg Phe Gly Asn Leu Lys Asn Gly Val Asn Asp Ile Lys
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:86

<400> SEQUENCE: 86

Gly Asn Leu Lys Asn Gly Val Asn Asp Ile Lys Asn His Lys Trp
1               5                   10                  15

<210> SEQ ID NO 87
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(13)
<223> OTHER INFORMATION: Peptide_SEQ ID NO:87

<400> SEQUENCE: 87

Asn Gly Val Asn Asp Ile Lys Asn His Lys Trp Phe Ala
1               5                   10

<210> SEQ ID NO 88
<211> LENGTH: 15
<212> TYPE: PRT
<213> ORGANISM: Artificial Sequence -continued

```
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:88

<400> SEQUENCE: 88

Val Asn Asp Ile Lys Asn His Lys Trp Phe Ala Thr Thr Asp Trp
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:89

<400> SEQUENCE: 89

Lys Asn His Lys Trp Phe Ala Thr Thr Asp Trp Ile Ala Ile Tyr
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:90

<400> SEQUENCE: 90

Trp Phe Ala Thr Thr Asp Trp Ile Ala Ile Tyr Gln Arg Lys Val
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:91

<400> SEQUENCE: 91

Thr Asp Trp Ile Ala Ile Tyr Gln Arg Lys Val Glu Ala Pro Phe
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:92

<400> SEQUENCE: 92

Ala Ile Tyr Gln Arg Lys Val Glu Ala Pro Phe Ile Pro Lys Phe
1               5                   10                  15
```

```
<210> SEQ ID NO 93
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: Peptide_SEQ ID NO:93

<400> SEQUENCE: 93

Arg Lys Val Glu Ala Pro Phe Ile Pro Lys Phe Lys
1               5                   10

<210> SEQ ID NO 94
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:94

<400> SEQUENCE: 94

Lys Val Glu Ala Pro Phe Ile Pro Lys Phe Lys Gly Pro Gly Asp
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:95

<400> SEQUENCE: 95

Pro Phe Ile Pro Lys Phe Lys Gly Pro Gly Asp Thr Ser Asn Phe
1               5                   10                  15

<210> SEQ ID NO 96
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:96

<400> SEQUENCE: 96

Lys Phe Lys Gly Pro Gly Asp Thr Ser Asn Phe Asp Asp Tyr
1               5                   10

<210> SEQ ID NO 97
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(16)
<223> OTHER INFORMATION: Peptide_SEQ ID NO:97
```

-continued

```
<400> SEQUENCE: 97

Gly Pro Gly Asp Thr Ser Asn Phe Asp Asp Tyr Glu Glu Glu Ile
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Peptide_SEQ ID NO:98

<400> SEQUENCE: 98

Ser Asn Phe Asp Asp Tyr Glu Glu Glu Ile Arg Val Ser Ile
1               5                   10                  15

<210> SEQ ID NO 99
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:99

<400> SEQUENCE: 99

Asp Tyr Glu Glu Glu Glu Ile Arg Val Ser Ile Asn Glu Lys
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: Peptide_SEQ ID NO:100

<400> SEQUENCE: 100

Glu Glu Glu Ile Arg Val Ser Ile Asn Glu Lys Cys Gly Lys
1               5                   10

<210> SEQ ID NO 101
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(16)
<223> OTHER INFORMATION: Peptide_SEQ ID NO:101

<400> SEQUENCE: 101

Ile Arg Val Ser Ile Asn Glu Lys Cys Gly Lys Glu Phe Ser Glu Phe
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(15)
<223> OTHER INFORMATION: Peptide_SEQ ID NO:102

<400> SEQUENCE: 102

Glu Asp Phe Leu Lys Lys Trp Glu Ser Pro Ala Gln Asn Thr Ala
1               5                   10                  15

<210> SEQ ID NO 103
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(13)
<223> OTHER INFORMATION: Peptide_SEQ ID NO:103

<400> SEQUENCE: 103

Lys Lys Trp Glu Ser Pro Ala Gln Asn Thr Ala His Leu
1               5                   10

<210> SEQ ID NO 104
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(17)
<223> OTHER INFORMATION: Peptide_SEQ ID NO:104

<400> SEQUENCE: 104

Ala Lys Arg Val Lys Gly Arg Thr Trp Thr Leu Cys Gly Arg Pro Glu
1               5                   10                  15

Ala
```